(12) United States Patent
Glenn, Jr. et al.

(10) Patent No.: US 8,765,170 B2
(45) Date of Patent: *Jul. 1, 2014

(54) PERSONAL CARE COMPOSITION IN THE FORM OF AN ARTICLE

(75) Inventors: Robert Wayne Glenn, Jr., Liberty Township, OH (US); Christopher Todd Morrissey, Mason, OH (US); Lee Arnold Schechtman, Fairfield, OH (US); Renee Danielle Bolden, Hamilton, OH (US); Kathleen Mary Kaufman, Cincinnati, OH (US); Lisa Jo Bartz, Cincinnati, OH (US); Thomas Edward Dufresne, Morrow, OH (US); Darren Paul Trokhan, Hamilton, OH (US); James Merle Heinrich, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 819 days.

This patent is subject to a terminal disclaimer.

(21) Appl. No.: 12/361,634

(22) Filed: Jan. 29, 2009

(65) Prior Publication Data

US 2009/0232873 A1 Sep. 17, 2009

Related U.S. Application Data

(60) Provisional application No. 61/024,728, filed on Jan. 30, 2008.

(51) Int. Cl.
*A61K 9/70* (2006.01)

(52) U.S. Cl.
USPC .................................................. 424/443

(58) Field of Classification Search
None
See application file for complete search history.

(56) References Cited

U.S. PATENT DOCUMENTS

| | | | |
|---|---|---|---|
| 2,356,168 A | 8/1944 | Mabley |
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 2,694,668 A | 11/1954 | Fricke |
| 2,809,971 A | 10/1957 | Bernstein |
| 3,152,046 A | 10/1964 | Kapral |
| 3,236,733 A | 2/1966 | Karsten |
| 3,321,425 A | 5/1967 | Blau |
| 3,332,880 A | 7/1967 | Kessler |
| 3,426,440 A | 2/1969 | Shen |

(Continued)

FOREIGN PATENT DOCUMENTS

| | | |
|---|---|---|
| CN | 1138091 A | 12/1996 |
| CN | 1219388 A | 6/1999 |

(Continued)

OTHER PUBLICATIONS

*M. K. Industires* (Gujarat India, http://www.soapstrips.com).

(Continued)

*Primary Examiner* — Mina Haghighatian
*Assistant Examiner* — Erin Hirt
(74) *Attorney, Agent, or Firm* — Angela K. Haughey

(57) ABSTRACT

Personal care compositions, especially those personal care compositions in the form of an article that is a porous, dissolvable solid structure.

2 Claims, 7 Drawing Sheets

(56) References Cited

U.S. PATENT DOCUMENTS

| | | |
|---|---|---|
| 3,489,688 A | 1/1970 | Pospischil |
| 3,653,383 A | 4/1972 | Wise |
| 3,695,989 A | 10/1972 | Albert |
| 3,753,196 A | 8/1973 | Kurtz |
| 3,761,418 A | 9/1973 | Parran, Jr. |
| 3,929,678 A | 12/1975 | Laughlin |
| 3,967,921 A | 7/1976 | Haberli |
| 4,020,156 A | 4/1977 | Murray |
| 4,051,081 A | 9/1977 | Jabs |
| 4,089,945 A | 5/1978 | Brinkman |
| 4,149,551 A | 4/1979 | Benjamin et al. |
| 4,196,190 A | 4/1980 | Gehman |
| 4,197,865 A | 4/1980 | Jacquet |
| 4,206,196 A | 6/1980 | Davis |
| 4,217,914 A | 8/1980 | Jacquet |
| 4,272,511 A | 6/1981 | Papantoniou |
| 4,323,683 A | 4/1982 | Bolich, Jr. |
| 4,345,080 A | 8/1982 | Bolich, Jr. |
| 4,379,753 A | 4/1983 | Bolich, Jr. |
| 4,381,919 A | 5/1983 | Jacquet |
| 4,422,853 A | 12/1983 | Jacquet |
| 4,470,982 A | 9/1984 | Winkler |
| 4,507,280 A | 3/1985 | Pohl |
| 4,529,586 A | 7/1985 | De Marco |
| 4,565,647 A | 1/1986 | Llenado |
| 4,663,158 A | 5/1987 | Wolfram |
| 4,710,374 A | 12/1987 | Grollier |
| 4,822,613 A | 4/1989 | Rodero |
| 4,885,107 A | 12/1989 | Wetzel |
| 4,976,953 A | 12/1990 | Orr |
| 4,990,280 A | 2/1991 | Thorengaard |
| 5,055,384 A | 10/1991 | Kuhnert |
| 5,061,481 A | 10/1991 | Suzuki |
| 5,062,889 A | 11/1991 | Hohl |
| 5,094,853 A | 3/1992 | Hagarty |
| 5,100,657 A | 3/1992 | Ansher-Jackson |
| 5,100,658 A | 3/1992 | Bolich, Jr. |
| 5,104,646 A | 4/1992 | Bolich, Jr. |
| 5,106,609 A | 4/1992 | Bolich, Jr. |
| 5,166,276 A | 11/1992 | Hayama |
| 5,220,033 A | 6/1993 | Kamei |
| 5,261,426 A | 11/1993 | Kellett et al. |
| 5,280,079 A | 1/1994 | Allen |
| RE34,584 E | 4/1994 | Grote |
| 5,391,368 A | 2/1995 | Gerstein |
| 5,409,703 A | 4/1995 | McAnalley |
| 5,429,628 A | 7/1995 | Trinh |
| 5,457,895 A | 10/1995 | Thompson |
| 5,476,597 A | 12/1995 | Sakata |
| 5,580,481 A | 12/1996 | Sakata |
| 5,582,786 A | 12/1996 | Brunskill |
| 5,660,845 A | 8/1997 | Trinh |
| 5,672,576 A | 9/1997 | Behrens |
| 5,674,478 A | 10/1997 | Dodd |
| 5,750,122 A | 5/1998 | Evans |
| 5,780,047 A | 7/1998 | Kamiya |
| 5,955,419 A | 9/1999 | Barket, Jr. |
| 5,976,454 A | 11/1999 | Sterzel et al. |
| 6,010,719 A | 1/2000 | Remon |
| 6,106,849 A | 8/2000 | Malkan |
| 6,177,391 B1 | 1/2001 | Zafar |
| 6,200,949 B1 | 3/2001 | Reijmer |
| 6,365,142 B1 | 4/2002 | Tamura |
| 6,458,754 B1 | 10/2002 | Velazquez |
| 6,503,521 B1 | 1/2003 | Atis |
| 6,525,034 B2 | 2/2003 | Dalrymple et al. |
| 6,790,814 B1 | 9/2004 | Marin |
| 6,800,295 B2 | 10/2004 | Fox |
| 6,808,375 B2 | 10/2004 | Klotzer |
| 6,825,161 B2 | 11/2004 | Shefer et al. |
| 6,831,046 B2 | 12/2004 | Carew et al. |
| 6,846,784 B2 | 1/2005 | Engel |
| 6,943,200 B1 | 9/2005 | Corrand |
| 7,015,181 B2 | 3/2006 | Lambino |
| 7,208,460 B2 | 4/2007 | Shefer et al. |
| 7,285,520 B2 | 10/2007 | Krzysik |
| 7,387,787 B2 | 6/2008 | Fox |
| 7,846,462 B2 | 12/2010 | Spadini et al. |
| 7,901,696 B2 | 3/2011 | Eknoian |
| 8,197,830 B2 | 6/2012 | Helfman et al. |
| 8,268,764 B2 | 9/2012 | Glenn, Jr. et al. |
| 8,273,333 B2 | 9/2012 | Glenn et al. |
| 8,288,332 B2 | 10/2012 | Fossum et al. |
| 8,309,505 B2 | 11/2012 | Fossum et al. |
| 8,349,341 B2 | 1/2013 | Glenn, Jr. et al. |
| 8,349,786 B2 | 1/2013 | Glenn et al. |
| 8,349,787 B2 | 1/2013 | Glenn et al. |
| 8,415,287 B2 | 4/2013 | Glenn, Jr. et al. |
| 8,461,090 B2 | 6/2013 | Glenn, Jr. et al. |
| 8,461,091 B2 | 6/2013 | Glenn, Jr. et al. |
| 8,466,099 B2 | 6/2013 | Glenn, Jr. et al. |
| 8,476,211 B2 | 7/2013 | Glenn, Jr. et al. |
| 8,546,640 B2 | 10/2013 | Popovsky et al. |
| 2002/0064510 A1 | 5/2002 | Dalrymple et al. |
| 2002/0077264 A1 | 6/2002 | Roberts et al. |
| 2002/0081930 A1 | 6/2002 | Jackson |
| 2002/0098994 A1 | 7/2002 | Zafar |
| 2002/0099109 A1 | 7/2002 | Dufton |
| 2002/0177621 A1 | 11/2002 | Hanada |
| 2002/0187181 A1 | 12/2002 | Godbey |
| 2003/0032573 A1 | 2/2003 | Tanner |
| 2003/0045441 A1 | 3/2003 | Hsu |
| 2003/0069154 A1 | 4/2003 | Hsu |
| 2003/0080150 A1 | 5/2003 | Cowan |
| 2003/0099691 A1 | 5/2003 | Lydzinski |
| 2003/0099692 A1 | 5/2003 | Lydzinski |
| 2003/0180242 A1* | 9/2003 | Eccard et al. .............. 424/70.11 |
| 2003/0186826 A1* | 10/2003 | Eccard et al. ................. 510/130 |
| 2003/0194416 A1 | 10/2003 | Shefer |
| 2003/0199412 A1 | 10/2003 | Gupta |
| 2003/0207776 A1 | 11/2003 | Shefer |
| 2003/0209166 A1 | 11/2003 | Vanmaele et al. |
| 2003/0215522 A1 | 11/2003 | Johnson |
| 2003/0232183 A1 | 12/2003 | Dufton |
| 2004/0029762 A1 | 2/2004 | Hensley |
| 2004/0032859 A1 | 2/2004 | Mino |
| 2004/0048759 A1 | 3/2004 | Ribble |
| 2004/0053808 A1 | 3/2004 | Raehse |
| 2004/0071742 A1 | 4/2004 | Popplewell |
| 2004/0071755 A1 | 4/2004 | Fox |
| 2004/0108615 A1 | 6/2004 | Foley |
| 2004/0110656 A1 | 6/2004 | Casey |
| 2004/0126585 A1 | 7/2004 | Kerins |
| 2004/0175404 A1 | 9/2004 | Shefer |
| 2004/0202632 A1 | 10/2004 | Gott |
| 2004/0206270 A1 | 10/2004 | Vanmaele |
| 2004/0242097 A1 | 12/2004 | Hasenoehrl et al. |
| 2004/0242772 A1 | 12/2004 | Huth |
| 2005/0069575 A1 | 3/2005 | Fox |
| 2005/0118237 A1 | 6/2005 | Krzysik |
| 2005/0136780 A1 | 6/2005 | Clark |
| 2005/0137272 A1 | 6/2005 | Gaserod |
| 2005/0202992 A1 | 9/2005 | Grandio Portabales |
| 2005/0220745 A1 | 10/2005 | Lu |
| 2005/0232954 A1 | 10/2005 | Yoshinari |
| 2005/0272836 A1 | 12/2005 | Yaginuma |
| 2005/0287106 A1 | 12/2005 | Legendre |
| 2006/0002880 A1 | 1/2006 | Peffly |
| 2006/0013869 A1 | 1/2006 | Ignatious et al. |
| 2006/0052263 A1 | 3/2006 | Roreger |
| 2006/0228319 A1 | 10/2006 | Vona |
| 2007/0028939 A1 | 2/2007 | Mareri |
| 2007/0149435 A1 | 6/2007 | Koenig |
| 2007/0225388 A1 | 9/2007 | Cooper |
| 2008/0035174 A1 | 2/2008 | Aubrun-Sonneville |
| 2008/0083420 A1 | 4/2008 | Glenn et al. |
| 2008/0090939 A1 | 4/2008 | Netravali |
| 2008/0131695 A1 | 6/2008 | Aouad |
| 2008/0138492 A1 | 6/2008 | Cingotti |
| 2008/0152894 A1 | 6/2008 | Beihoffer |
| 2008/0215023 A1 | 9/2008 | Scavone |
| 2008/0292669 A1 | 11/2008 | Deng et al. |
| 2008/0293839 A1 | 11/2008 | Stobby |
| 2009/0263342 A1* | 10/2009 | Glenn et al. .............. 424/70.11 |

(56) References Cited

U.S. PATENT DOCUMENTS

| | | | | |
|---|---|---|---|---|
| 2010/0167971 A1* | 7/2010 | Glenn et al. | | 510/101 |
| 2010/0173817 A1* | 7/2010 | Glenn et al. | | 510/120 |
| 2010/0179083 A1* | 7/2010 | Glenn et al. | | 510/120 |
| 2010/0279905 A1* | 11/2010 | Glenn et al. | | 510/103 |
| 2010/0286011 A1* | 11/2010 | Glenn et al. | | 510/120 |
| 2010/0291165 A1 | 11/2010 | Glenn, Jr. | | |
| 2010/0298188 A1* | 11/2010 | Glenn et al. | | 510/120 |
| 2011/0023240 A1* | 2/2011 | Fossum et al. | | 8/137 |
| 2011/0027328 A1 | 2/2011 | Baig et al. | | |
| 2011/0028373 A1* | 2/2011 | Fossum et al. | | 510/236 |
| 2011/0028374 A1* | 2/2011 | Fossum et al. | | 510/296 |
| 2011/0182956 A1 | 7/2011 | Glenn, Jr. | | |
| 2011/0189246 A1 | 8/2011 | Glenn, Jr. | | |
| 2011/0189247 A1 | 8/2011 | Glenn, Jr. | | |
| 2011/0195098 A1 | 8/2011 | Glenn, Jr. | | |
| 2011/0250256 A1 | 10/2011 | Hyun-Oh et al. | | |
| 2012/0021026 A1 | 1/2012 | Chhabra | | |
| 2012/0270029 A1 | 10/2012 | Granberg et al. | | |
| 2012/0321580 A1 | 12/2012 | Glenn, Jr. et al. | | |
| 2013/0236520 A1 | 9/2013 | Popovsky et al. | | |

FOREIGN PATENT DOCUMENTS

| | | |
|---|---|---|
| CN | 1268558 A | 10/2000 |
| CN | 1357613 A | 7/2002 |
| CN | 1530431 A | 9/2004 |
| CN | 1583991 A | 2/2005 |
| DE | 19607851 A1 | 9/1997 |
| DE | 10331767 A1 | 2/2005 |
| EP | 609808 A1 | 8/1994 |
| EP | 0858828 A1 | 8/1998 |
| EP | 1160311 B1 | 12/2001 |
| EP | 1217987 B1 | 12/2004 |
| EP | 1958532 A2 | 8/2008 |
| EP | 1958532 A2 | 8/2008 |
| EP | 2085434 A1 | 8/2009 |
| FR | 2871685 A | 12/2005 |
| FR | 2886845 A | 12/2006 |
| GB | 2235204 A | 2/1991 |
| GB | 2355008 A | 4/2001 |
| JP | 58021608 A | 2/1983 |
| JP | 58216109 A | 12/1983 |
| JP | 62-081432 | 4/1987 |
| JP | 62072609 A | 4/1987 |
| JP | 62072610 A | 4/1987 |
| JP | 1313418 A | 12/1989 |
| JP | 5344873 A | 12/1993 |
| JP | 6017083 A | 1/1994 |
| JP | 07-53349 | 2/1995 |
| JP | 7089852 A | 4/1995 |
| JP | 8325133 A | 12/1996 |
| JP | 10251371 A | 9/1998 |
| JP | 2003073700 A | 3/2003 |
| JP | 2003082397 A | 3/2003 |
| JP | 2004345983 A | 12/2004 |
| JP | 2005171063 A | 6/2005 |
| JP | 2007197540 A | 8/2007 |
| JP | 2007091954 A | 12/2007 |
| KR | 20020003442 | 1/2002 |
| WO | WO9514495 A1 | 6/1995 |
| WO | 01/19948 A1 | 3/2001 |
| WO | 01/25322 A1 | 4/2001 |
| WO | 01/25393 A1 | 4/2001 |
| WO | WO 0124770 A1 | 4/2001 |
| WO | 01/54667 A1 | 8/2001 |
| WO | WO 2004/032859 A | 4/2004 |
| WO | WO2004/041991 A1 | 5/2004 |
| WO | WO 2005003423 A1 | 1/2005 |
| WO | WO2007033598 A1 | 3/2007 |
| WO | WO2007/093558 A2 | 8/2007 |
| WO | WO2009019571 | 2/2009 |

OTHER PUBLICATIONS

*Sanipro Sanitary Products* (Italy, http://www.sanipro.it).
*Adhesives Research* (Pennsylvania, http://12.4.33.51/news/apresmed.htm).
*Solublon* (Toyohashi Japan, http://www.solublon.com).
*SPI Pharma* (Delaware, http://www.spipharma.com).
*Wenda* (China, http://www.wenda.com).
*MOVA Pharmaceutical and Kosmos* (USA, http:www.icon-pr.com/news/news_print.cfm?inv_id=266-1).
*Cima Labs, Inc.* (Minnesota, http://www.cimalabs.com/).
*Cardinal Health* (Dublin, Ohio, http://spd.cardinal.com/).
*Le Laboratoire du Bain* (France, http://www.labodubain.com/).
*Amerilab Technologies, Inc.* (Minnesota, http://www.amerilabtech.com/).
*Meguiar's Car Wash Strips*: (Meguiar's Inc. California, http://www.automotivedigest.com/view_art.asp?articlesID=12414).
*Pure Soap Leafz*: (Soap UNLTD, Netherlands, http://www.upandunder.co.uk/eshop/catalogue/testbs.asp?Manufacturer_ID=252&Activity_ID=33&Description_ID=157).
*Dissolving Soap Strips* (Ranir LLC, Michigan, www.ranir.com).
*Japanese Paper Soap* (http://www.wishingfish.com/papersoap.html).
*Travelers Passport Paper Soap Sheets* (http://www.weddingfavorsnow.com/index.asp?PageAction=VIEWPROD&ProdID=510).
P&G Case 11200M ISR dated May 6, 2011, PCT/US2009/067130, 5 pages.
P&G Case 11201M ISR dated May 4, 2011, PCT/US2009/067088, 5 pages.
P&G Case 11201M ISR dated Jul. 19, 2011, PCT/US2009/067088, 7 pages.
P&G Case 11202M3 ISR dated May 9, 2011, PCT/US2009/067132, 5 pages.
P&G Case 11202M2 ISR dated Jul. 20, 2011, PCT/US2009/067131, 5 pages.
P&G Case 11202M ISR dated Apr. 29, 2011, PCT/US2009/067089, 5 pages.
P&G Case 11037M ISR dated Aug. 17, 2009, PCT/US2009/040739, 6 pages.
P&G Case 11037M ISR dated Nov. 4, 2009, PCT/US2009/040739, 10 pages.
P&G Case 11199M ISR dated Dec. 15, 2011, PCT/US2009/067087, 5 pages.
P&G Case 11203M ISR dated Jul. 19, 2011, PCT/US2009/067133, 4 pages.
P&G Case 11200M ISR dated Jul. 19, 2011, PCT/US2009/067130, 7 pages.
P&G Case 11494M ISR dated Apr. 27, 2011, PCT/US2010/059365, 5 pages.
P&G Case 11495M ISR dated Apr. 27, 2011, PCT/US2010/059455, 5 pages.
P&G Case 11523M ISRr dated Apr. 27, 2011, PCT/US2010/059359, 5 pages.
T. Hildebrand, P. Rüegsegger. "Quantification of bone microarchitecture with the structure model index." Computer Methods in Biomechanics and Biomedical Engineering 1997; 1:15-23.
Vesterby, A.; Star volume in bone research. A histomorphometric analysis of trabecular bone structure using vertical sections; Anat Rec.; Feb. 1993; 235(2): 325-334.
C. D. Vaughan. Solubility, Effects in Product, Package, Penetration and Preservation, Cosmetics and Toiletries, vol. 103, Oct. 1988.
*Encyclopedia of Polymer Science and Engineering*, vol. 15, 2d ed., pp. 204-308, John Wiley & Sons, Inc. (1989).
Anonymous: "P8136 Poly(vinyl alcohol)" Internet article, [Online] XP002538935 Retrieved from the Internet: URL:http://www.sigmaaldrich.com/catalog/ProductDetail.do?D7=0&N25=SEARCH_CONCAT_PNO%7CBRAND_KEY&N4=P8136%7CSIAL&N25=0&Qs=0N&F=SPEC> [retrieved on Jul. 28, 2009].
All Office Actions, U.S. Appl. No. 12/633,228.
U.S. Appl. No. 13/440,475, filed Apr. 5, 2012, Granberg et al.
U.S. Appl. No. 13/597,539, filed Aug. 29, 2012, Glenn, Jr. et al.
U.S. Appl. No. 13/561,298, filed Jul. 30, 2012, Glenn, Jr. et al.
All Office Actions, U.S. Appl. No. 13/597,539.
All Office Actions, U.S. Appl. No. 13/915,797.

(56) References Cited

OTHER PUBLICATIONS

All Office Actions, U.S. Appl. No. 13/561,298.
P&G Case 12068M ISR dated Jul. 20, 2012, PCT/US2012/032253, 5 pages.
All Office Actions, U.S. Appl. No. 12/424,812.
All Office Actions, U.S. Appl. No. 12/633,257.
All Office Actions, U.S. Appl. No. 12/633,301.
All Office Actions, U.S. Appl. No. 12/633,550.
All Office Actions, U.S. Appl. No. 12/633,335.
All Office Actions, U.S. Appl. No. 12/633,415.
All Office Actions, U.S. Appl. No. 12/633,572.
All Office Actions, U.S. Appl. No. 12/962,846.
All Office Actions, U.S. Appl. No. 12/962,873.
All Office Actions, U.S. Appl. No. 12/962,888.
All Office Actions, U.S. Appl. No. 12/962,905.
All Office Actions, U.S. Appl. No. 13/173,639.
All Office Actions, U.S. Appl. No. 13/440,475.
P&G Case 11496M ISR dated Jun. 7, 2013, PCT/US2010/059441, 9 pages.

* cited by examiner

PERSONAL CARE COMPOSITION IN THE FORM OF AN ARTICLE

FIELD OF THE INVENTION

The present invention relates to personal care compositions, especially those personal care compositions in the form of an article that is a porous, dissolvable solid structure.

BACKGROUND OF THE INVENTION

The majority of personal care products in the market today are sold as liquid products. While widely used, liquid products have disadvantages in terms of packaging, storage, transportation, and convenience of use.

Liquid personal care products typically are sold in bottles which add significant cost as well as packaging waste, much of which ends up in land-fills. Liquid personal care products also usually comprise a substantial amount of water in the formula which adds significant weight and size translating into greater shipping and storage costs. Liquid personal care products can also be difficult to use in terms of controlling dosage and the delivery of the product.

Dissolvable personal care films are known comprising a water-soluble polymeric structurant and a surfactant or other active ingredient. However, in order to achieve the requisite rapid dissolution rates needed for consumer convenience, these films are generally on the order of less than 100 microns thickness (typically 50 microns) and, thereby, are generally of too low a basis weight (typically 50-100 grams of solid per square meter) to enable feasible consumer application of a sufficient dosage of active ingredients for entire body or whole head hair application and performance, i.e., beyond lower dosage applications such as hand cleansing and/or the facial applications.

Dissolvable porous solid personal care products have been taught comprising natural starch and surfactants (See US 2004/0048759). However, these porous solids were produced by an anhydrous extrusion process and employing volatile blowing agents to produce the cellular structure via high pressure drop induced expansion of the solid. The anhydrous process limits the components available to anhydrous materials such as solid-sourced surfactants which are unacceptably harsh to skin, hair and fabric surfaces and are known for "skin" formation due to the partial collapse of structure after the abrupt high pressure drop at the exit of the extruder die also termed "shrinkage". Such skins are unacceptable as these would serve as a barrier for water ingress to the interior and adversely affect dissolution rates.

Freeze-dried open-celled porous solids for personal care have been taught (See U.S. Pat. No. 6,106,849 and US 2007/0225388). However, such resulting freeze-dried porous solids are rigid, brittle and fragile and without plasticization of the polymer such that it remains in its glassy state to avoid collapse of the structure during the process (See U.S. Pat. No. 5,457,895 Kearney P. et. al., issued 1995). Also, freeze-drying is a relatively high energy and costly process.

Therefore a need exists for a process that results in a desired flexible, dissolvable porous solid structure which can be easily and quickly manufactured that gives the desired properties of flexibility, dissolution, surfactant dosing levels and lather by consumers utilizing such articles.

It is therefore an object of the present invention to provide a dissolvable solid personal care product that can be conveniently and quickly dissolved in the palm of the consumer to reconstitute a liquid product for ease of application to hair/skin while providing sufficient topical delivery of active agents for whole head hair and whole body skin applications (with similar performance as today's liquid products). It is a further object of the present invention to provide such a product that can be produced in an economical manner by physical aeration followed by subsequent drying. It is an even further object of the present invention to provide such a product with desirable softness and flexibility.

SUMMARY OF THE INVENTION

The present invention relates to a personal care article comprising: from about 23% to about 75% surfactant; from about 10% to about 50% water soluble polymer; and optionally, from about 1% to about 15% plasticizer; such that the article is in the form of a flexible porous dissolvable solid structure, wherein said article has a % open cell content of from about 80% to about 100%.

In yet another aspect, the present invention relates to a process comprising the steps of: Preparing a pre-mix comprising surfactant, water soluble polymer, and optionally plasticizer, wherein said pre-mix has: from about 15% to 40% solids; and a viscosity of from about 2,500 cps to 30,000 cps; aerating said pre-mix by introducing a gas into the pre-mix to form a wet aerated pre-mix; forming the wet aerated pre-mix into a desired one or more shapes to form shaped wet pre-mix; and drying the shaped wet pre-mix to a desired final moisture content to form a porous dissolvable solid structure.

In particular embodiments, the personal care article has a cellular interconnectivity defined by a porous solid with a Star Volume of from about 1 $mm^3$ to about 90 $mm^3$; and a Structure Model Index that is non-negative and ranges from about 0.0 to about 3.0.

In some embodiments, the article has a Cell Wall Thickness of from about from about 0.02 mm to about 0.015 mm; and a Specific Surface Area of from about 0.03 $m^2/g$ to about 0.25 $m^2/g$.

DETAILED DESCRIPTION OF THE INVENTION

Figure 1:
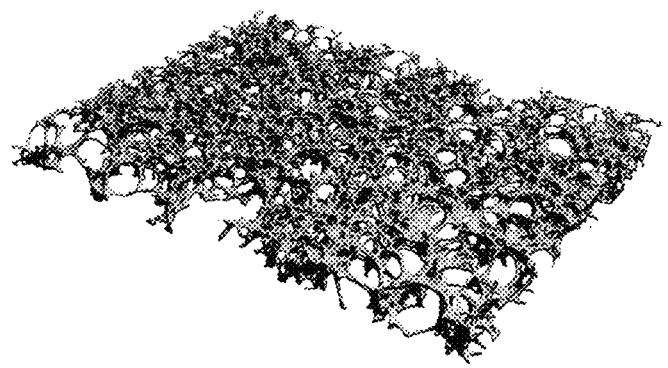
FIG. 1 is a micro computed tomography system image of Example 1 as discussed in Table 9

The present inventors have found that dissolvable solid personal care products can be prepared that can be conveniently and quickly dissolved in the palm of the consumer to reconstitute a liquid product for ease of application to hair and/or skin while providing sufficient topical delivery of active agents for whole head hair and whole body skin applications (with similar performance as conventional liquid products). It has also been found that such products can be produced in an economical manner by physical aeration followed by subsequent drying. Additionally, it has been found that such products can now be produced with desirable softness and flexibility.

The present inventors have surprisingly discovered that rapidly-dissolving porous solids with a predominantly open-celled structure can be produced via physical aeration followed by subsequent drying (as a more cost effective alternative to conventional freeze drying). This can be accomplished by creating a physically aerated wet foam with a controlled degree of foam instability during the drying process such that an optimum level of bubble breakage and coalescence occurs to generate a plurality of open channels and without collapse of the foam plateau border three dimensional structure during the drying process thereby maintaining the physical strength and cohesiveness of the porous solid.

It was surprising and non-intuitive to discover that this instability and coalescence could be controllably manipulated such that original closed-cell wet foam transforms within the multi-hour drying process into a true open-celled porous structure wherein the plurality of open-channels extend to the solid's surface. Indeed, the vast majority of original attempts by the present inventors led to either stable wet foams drying to conventional closed-cell solid foams or unstable wet foams drying to collapsed films. It has been further discovered that such open-celled dissolvable porous solids prepared by physical aeration followed by drying can only be prepared within specific rheological and compositional ranges (% solids). Moreover, it has been discovered that such open-celled dissolvable porous solids can be prepared with significant plasticizer levels for desirable softness and flexibility.

The flexible porous dissolvable solid structure article may be referred to herein as "the Article" or "the Dissolvable Article". All references are intended to mean the flexible dissolvable porous solid structure article.

As used herein, "flexible" means that the porous dissolvable solid structure article meets the distance to maximum force values of from about 6 mm to about 30 mm, in one embodiment from about 7 mm to about 25 mm, in another embodiment from about 8 mm to about 20 mm, and in still another embodiment from about 9 mm to about 15 mm as measured by the Distance to Maximum Force Method.

As used herein, "dissolvable" means that the flexible porous dissolvable solid structure article meets the hand dissolution value. The Article has a hand dissolution value of from about 1 to about 30 strokes, in one embodiment from about 2 to about 25 strokes, in another embodiment from about 3 to about 20 strokes, and in still another embodiment from about 4 to about 15 strokes as measured by the Hand Dissolution Method.

As used herein "porous solid structure" means a solid, interconnected, polymer-containing matrix that defines a network of spaces or cells that contain the gas of the surrounding atmosphere, typically air. The interconnectivity of the structure may be described by a Star Volume, a Structure Model Index (SMI) or a Percent Open Cell Content.

The Article has a Star Volume of from about 1 mm$^3$ to about 90 mm$^3$, in one embodiment from about 5 mm$^3$ to about 80 mm$^3$, in another embodiment from about 10 mm$^3$ to about 70 mm$^3$, and in still another embodiment from about 15 mm$^3$ to about 60 mm$^3$. The Article has a non-negative Structure Model Index of from about 0.0 to about 3.0, in one embodiment from about 0.5 to about 2.75, and in another embodiment from about 1.0 to about 2.50. The Article has a Percent Open Cell Content of from about 80% to 100%, in one embodiment from about 85% to about 97.5%, and in another embodiment from about 90% to about 95%.

To measure the cell interconnectivity via the Star Volume and the Structure Model Index, disk-like samples, approximately 4 cm in diameter and 3 to 7 mm high, are scanned using a micro computed tomography system (μCT80, SN 06071200, Scanco Medical AG). Each sample is imaged while sitting flat on the bottom of a cylindrical tube. Image acquisition parameters are 45 kVp, 177 μA, 51.2 mm field of view, 800 ms integration time, 1000 projections. The number of slices is adjusted to cover the height of the sample. The reconstructed data set consisted of a stack of images, each 2048×2048 pixels, with an isotropic resolution of 25 μm. For data analysis, a volume of interest is selected to be fully within the sample, avoiding the surface region. A typical volume of interest is 1028×772×98 voxels.

Structure Model Index (SMI) is measured using Scanco Medical's Bone Trabecular Morphometry evaluation with a threshold of 17. With this index the structural appearance of trabecular bone is quantified (see T. Hildebrand, P. Rüegsegger. Quantification of bone microarchitecture with the structure model index. *Comp Meth Biomech Biomed Eng* 1997; 1:15-23). The triangulated surface is dilated in normal direction by an infinitesimal amount, and the new bone surface and volume is calculated. By this, the derivative of the bone surface (dBS/dr) can be determined. The SMI is then represented by the equation:

$$SMI = 6 \cdot \frac{BV \cdot \frac{dBS}{dr}}{BS^2}$$

SMI relates to the convexity of the structure to a model type. Ideal (flat) plates have an SMI of 0 (no surface change with dilation of the plates), whereas ideal cylindrical rods have an SMI of 3 (linear increase in surface with dilation of rods). Round spheres have an SMI of 4. Concave structure gives negative dBS/dr, resulting in negative SMI values. Artificial boundaries at the edge of the volume of interest are not included in the calculation and thus suppressed.

In addition to the Scanco Medical Analysis, Star Volume measurements are made. Star Volume is a measure of the "openness" of the void space in a two phase structure. By choosing a random uniformly distributed set of points in the phase of interest (in this case the phase of interest is the void space or air), lines can be extended in random directions from each of these points. The lines are extended until they touch the foreground phase. The length of each of these lines is then recorded. The random points have a sampling of 10 in each direction (x/y/z) and at each point 10 random angles are chosen. If the line extends to the border of the ROI of interest that line is discarded (only accept lines that actually intersect with the foreground phase). The final equation is based upon the research entitled *Star Volume In Bone Research A Histomorphometric Analysis Of Trabecular Bone Structure Using Vertical Sections*; Vesterby, A.; Anat Rec.; 1993 February; 235(2):325-334:

$$StarVolume = \frac{4}{3}\pi \cdot \frac{\sum dist^3}{N}$$

where "dist" is the individual distances and N is the number of lines examined.

The Percent Open Cell Content is measured via gas pycnometry. Gas pycnometry is a common analytical technique that uses a gas displacement method to measure volume accurately. Inert gases, such as helium or nitrogen, are used as the displacement medium. The sample is sealed in the instrument compartment of known volume, the appropriate inert gas is admitted, and then expanded into another precision internal volume. The pressure before and after expansion is measured and used to compute the sample volume. Dividing this volume into the sample weight gives the gas displacement density. ASTM Standard Test Method D2856 provides a procedure for determining the percentage of open cells using an older model of an air comparison pycnometer. This device is no longer manufactured. However, you can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials. The samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the true volume as measured by the Accupyc. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde Orr and Paul Webb.

The Article has a maximum Cell Wall Thickness. The Article has a Cell Wall Thickness of from about from about 0.02 mm to about 0.015 mm, in one embodiment from about 0.025 mm to about 0.012 mm, in another embodiment from about 0.03 mm to about 0.09 mm, and in still another embodiment from about 0.035 mm to about 0.06 mm.

The Cell Wall Thickness is computed from the scanned images via a micro computed tomography system (μCT80, SN 06071200, Scanco Medical AG) as described herein. The Cell Wall Thickness is determined according to the method defined for the measurement of Trabecular Thickness using Scanco Medical's Bone Trabecular Morphometry evaluation. The definition of Trabecular Thickness as taken from the Scanco User's manual: Trabecular Thickness uses a Euclidean distance transformation (EDM), which calculates the Euclidean distance from any point in the foreground to the nearest background point. The Trabecular Thickness measure represents twice the centerline values associated with the local maxima of the EDM, which represents the distance to the center of the object (twice this distance will yield the thickness).

The Article also has a minimum Specific Surface Area. The Article has a Specific Surface Area of from about 0.03 $m^2/g$ to about 0.25 $m^2/g$, in one embodiment from about 0.035 $m^2/g$ to about 0.22 $m^2/g$, in another embodiment from about 0.04 $m^2/g$ to about 0.19 $m^2/g$, and in still another embodiment from about 0.045 $m^2/g$ to about 0.16 $m^2/g$.

The Specific Surface Area is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the combined weight of the degassed sample and the sample tube. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved. Samples may then analyzed using an ASAP 2420 with krypton gas adsorption.

It is recommended that the gas adsorption and pyncnomeetry measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde Orr and Paul Webb.

The Article is preferably a flat, flexible substrate in the form of a pad, a strip or tape and having a thickness of from about 1.0 mm to about 10 mm, in one embodiment from about 2 mm to about 9 mm, in another embodiment from about 3 mm to about 8 mm, and in a further embodiment from about 4 mm to about 7 mm as measured by the below methodology.

The thickness of the dissolvable porous solid (i.e., substrate or sample substrate) is obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 inch diameter platen weighing about 32 grams, which measures thickness at an application pressure of about 40.7 psi (6.32 $gm/cm^2$). In the case of cylindrical, spherical, or other objects with more of a third dimension versus a pad or strip, the thickness is taken as the maximum distance of the shortest dimension, i.e., the diameter of a sphere or cylinder for instance, and the thickness ranges are the same as described above. The thickness of the dissolvable porous solid is measured by raising the platen, placing a section of the sample substrate on the stand beneath the platen, carefully lowering the platen to contact the sample substrate, releasing the platen, and measuring the thickness of the sample substrate in millimeters on the digital readout. The sample substrate should be fully extended to all edges of the platen to make sure thickness is measured at the lowest possible surface pressure, except for the case of more rigid substrates which are not flat. For more rigid substrates which are not completely flat, a flat edge of the substrate is measured using only one portion of the platen impinging on the flat portion of the substrate.

The Article has a basis weight 125 $grams/m^2$ to about 1,000 $grams/m^2$, in another embodiment from about 150 $grams/m^2$ to about 800 $grams/m^2$, in an alternate embodiment from about 200 grams/m² to about 700 grams/m², and in still another embodiment from about 300 grams/m² to about 650 grams/m².

The Basis Weight of the dissolvable porous solid component of the personal care composition herein is calculated as the weight of the dissolvable porous solid component per area of the selected dissolvable porous solid (grams/m²). The area is calculated as the projected area onto a flat surface perpendicular to the outer edges of the porous solid. For a flat object, the area is thus computed based on the area enclosed within the outer perimeter of the sample. For a spherical object, the area is thus computed based on the average diameter as 3.14× (diameter/2)². For a cylindrical object, the area is thus computed based on the average diameter and average length as diameter×length. For an irregularly shaped three dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (preferably shaded-in for contrast) including a scale and using image analysis techniques.

The Article has a dry density of from about 0.03 g/cm³ to about 0.15 g/cm³, in one embodiment from about 0.04 g/cm³ to about 0.12 g/cm³, and in an alternate embodiment from about 0.06 g/cm³ to about 0.10 g/cm³.

The dry density of the dissolvable porous solid is determined by the equation: Calculated Density=Basis Weight of porous solid/(Porous Solid Thickness×1,000). The Basis Weight and Thickness of the dissolvable porous solid are determined in accordance with the methodologies described herein.

It has been surprisingly discovered by the present inventors that rapidly dissolving porous solids with a predominantly inter-connected, open-celled structure can be produced via physical aeration followed by subsequent drying (as a more cost-effective alternative to conventional freeze drying). This can be accomplished by creating a physically aerated wet foam with a controlled degree of instability during the drying process such that an optimum level of bubble breakage and coalescence occurs to generate a plurality of open channels, and without collapse of the three dimensional foam plateau border structure during the drying process, thereby maintaining the physical strength and cohesiveness of the porous solid. It was surprising and non-intuitive to discover that this instability and coalescence could be controllably manipulated such that the original closed-cell wet foam transforms within the multi-hour drying process into a true open-celled porous structure wherein the plurality of open channels extends to the solid's surface and with sufficient structural integrity. Indeed, the vast majority of original attempts by the present inventors led to either wet foams that were too stable drying to conventional closed-cell porous solids or wet foams that were too unstable drying to collapsed films.

It has been discovered that such open-celled dissolvable porous solids prepared by physical aeration followed by drying can only be achieved within a narrowly defined theological range as defined above. Achieving the relatively low viscosity range required is problematic due to the typically high polymeric structurant levels required for sufficient solid structure formation as well as at desired higher surfactant and % solids levels (for product compaction and sustainability). To achieve the required relatively low viscosity range of the present invention at relatively high surfactant and polymer levels while producing integral and cohesive solid structures, it has been discovered that several compositional strategies can be employed, either alone or in combination, including but not limited to: (i) employing water-soluble polymers within the requisite molecular weight range but with relatively low viscosity build as defined herein; (ii) deliberate dilution of the processing mixture with water; (iii) adding electrolyte or hydrotrope to manipulate the surfactant structure viscosity; or (iv) adding low molecular weight solvents to manipulate the viscosity. Importantly, aerating processing mixtures below the required viscosity range results in less desirable, low basis weight and non-cohesive porous solids.

It is also significant that the discovered processing mixture viscosity range of the present invention has been proven to produce rapidly dissolving open-celled porous solids independently of polymer type (including naturally derived) and surfactant system type as is demonstrated single-variably in Examples 6 through 19. This in itself is a surprising finding and goes against conventional wisdom that it is the polymer type, and specifically the molecular weight, that is the primary driver of solid dissolution (See US2003/0180242 by Eccard W. E. et. al.).

It has also been found that the above described characteristics of the present invention apply toward the production of open-celled porous structures employing either semi-continuous or continuous aeration equipment from the food industry that are used in the manufacture of marshmallows.

It has been surprisingly found that processing mixtures wherein the surfactant phase structure is in the form of lamellar liquid crystals (as opposed to isotropic thread-like micelles) produce porous solids with improved appearance and cohesiveness.

Unlike many solid-making processes such as extrusion, the above physical aeration and drying process of the present invention is not limited to solid-sourced surfactants which are typically more crystalline and have performance negatives (skin and scalp harshness and sensorial issues). Accordingly, at least about 10% of the surfactants, by weight of the substantially dry article, comprise surfactants with low crystallinity and having a Krafft temperature of less than about 40° C., and in another embodiment from about 0° C. to about 40° C., and in an alternate embodiment from about 0° C. to about 35° C. The Kraft point can be measured by preparing a 1% dispersion of the surfactant in water. If the surfactant is soluble at room temperature, the solution is cooled to 0° C. If the surfactant does not precipitate out, its Krafft point is considered to be less than 0° C. If it precipitates out, the solution is slowly warmed with stirring in a water bath. The temperature at which the precipitate dissolves is determined to be the Krafft point. If the Krafft point is above room temperature, the solution is first heated rapidly to dissolve all the surfactant. It is then cooled until precipitation occurs, and then slowly warmed to determine the Kraft point as described above. While not wishing to be bound by theory, it is believed that higher Krafft points are indicative of a surfactant being more crystalline and less soluble in an aqueous system. Krafft points for common surfactants can be referenced [Rosen M. J. (2004) "Surfactants and Interfacial Phenomena, $3^{rd}$ Edition", John Wiley & Sons, New Jersey. ISBN 0-471-47818-0]

"Personal care composition," as used herein, means a composition that may be applied to mammalian keratinous tissue without undue undesirable effects.

"Keratinous tissue," as used herein, means keratin-containing layers disposed as the outermost protective covering of mammals and includes, but is not limited to, skin, hair, scalp and nails.

"Beauty benefit," as used herein in reference to mammalian keratinous tissue includes, but is not limited to cleansing, sebum inhibition, reducing the oily and/or shiny appearance of skin and/or hair, reducing dryness, itchiness and/or flakiness, reducing skin pore size, exfoliation, desquamation, improving the appearance of the keratinous tissue, conditioning, smoothening, etc.

"Beauty benefit agent," as used herein, refers to materials that can be included in the composition to deliver one or more Beauty benefits.

"Skin care actives," or "actives," as used herein, means compounds that, when applied to the skin, provide a benefit or improvement to the skin. It is to be understood that skin care actives are useful not only for application to skin, but also to hair, scalp, nails and other mammalian keratinous tissue.

The dissolvable personal care porous solids of the present invention can be useful for treating keratinous tissue (e.g., hair, skin, or nails) condition. As use herein, "treating" or "treatment" or "treat" includes regulating and/or immediately improving keratinous tissue cosmetic appearance and/or feel. For instance, "regulating skin, hair, or nail condition" includes: thickening of skin, hair, or nails (e.g., building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair.

I. Composition

Surfactants

The Article comprises one or more surfactants suitable for application to the hair or skin. Surfactants suitable for use in the Article includes anionic surfactants, nonionic surfactants, cationic surfactants, zwitterionic surfactants, amphoteric surfactants, or combinations thereof.

The one or more surfactants may be present from about 23 wt % to about 75 wt % by weight of the Article of surfactant, in one embodiment from about 30 wt % to about 70 wt %, and in another embodiment from about 40 wt % to about 65 wt % by weight of the Article of surfactant.

The surfactant component may also include surfactant that are intended primarily as a process aid in making a stable foam structure, wherein the surfactant includes conventional surfactants or emulsifiers that need not provide any lathering performance. Examples of emulsifiers for use as a surfactant component herein include mono- and di-glycerides, fatty alcohols, polyglycerol esters, propylene glycol esters, sorbitan esters and other emulsifiers known or otherwise commonly used to stabilized air interfaces.

Anionic surfactants suitable include those described in McCutcheon's Detergents and Emulsifiers, North American Edition (1986), Allured Publishing Corp.; McCutcheon's, Functional Materials, North American Edition (1992), Allured Publishing Corp.; and U.S. Pat. No. 3,929,678 (Laughlin et al.).

Non-limiting examples of anionic surfactants suitable for use herein include alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

Anionic surfactants suitable include alkyl and alkyl ether sulfates. These materials have the respective formulae $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. The alkyl ether sulfates are typically made as condensation products of ethylene oxide and monohydric alcohol's having from about 8 to about 24 carbon atoms. Preferably, R has from about 10 to about 18 carbon atoms in both the alkyl and alkyl ether sulfates. Useful alcohols can be derived from fats, e.g., coconut oil or tallow, or can be synthetic. Lauryl alcohol and straight chain alcohol's derived from coconut oil are preferred herein. Such alcohol's are reacted with about 1 to about 10, preferably from about 3 to about 5, and especially about 3, molar proportions of ethylene oxide and the resulting mixture of molecular species having, for example, an average of 3 moles of ethylene oxide per mole of alcohol, is sulfated and neutralized. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants include water-soluble salts of the organic, sulfuric acid reaction products of the general formula $[R^1—SO_3-M]$, wherein $R^1$ is chosen from the group consisting of a straight or branched chain, saturated aliphatic hydrocarbon radical having from about 8 to about 24, preferably about 10 to about 18, carbon atoms; and M is a cation. Preferred are alkali metal and ammonium sulfonated $C_{10-18}$ n-paraffins.

Additional examples of suitable anionic surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other suitable anionic surfactants of this variety are described in U.S. Pat. Nos. 2,486,921, 2,486,922 and 2,396,278.

Still other suitable anionic surfactants are the succinamates, examples of which include disodium N-octadecylsulfosuccinamate; diammoniumlauryl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; and dioctyl esters of sodium sulfosuccinic acid.

Other suitable anionic surfactants include olefin sulfonates having about 12 to about 24 carbon atoms. The α-olefins from which the olefin sulfonates are derived are mono-olefins having about 12 to about 24 carbon atoms, preferably about 14 to about 16 carbon atoms. Preferably, they are straight chain olefins.

Another class of anionic surfactants suitable for use in the personal care compositions are the β-alkyloxy alkane sulfonates. These compounds have the following formula:

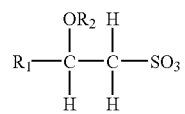

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Other suitable surfactants are described in *McCutcheon's, Emulsifiers and Detergents,* 1989 *Annual,* published by M. C. Publishing Co., and in U.S. Pat. No. 3,929,678.

Preferred anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Amphoteric surfactants suitable for use in the personal care compositions of the present invention includes those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378. Zwitterionic surfactants suitable for use include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Zwitterionic surfactants which are suitable include betaines, including cocoamidopropyl betaine.

The amphoteric surfactants suitable herein may also include alkylamphoacetates including lauroamphoacetate and cocoamphoacetate. Alkylamphoacetates can be comprised of monoacetates and diacetates. In some types of alkylamphoacetates, diacetates are impurities or unintended reaction products.

Cationic surfactants can also be utilized, but are generally less preferred, and preferably represent less than about 5% by weight of the Article.

Suitable nonionic surfactants include those described in McCutcheion's Detergents and Emulsifiers, North American edition (1986), Allured Publishing Corp., and McCutcheion's Functional Materials, North American edition (1992). These nonionic surfactants suitable for use herein include alkyl glucosides, alkyl polyglucosides, polyhydroxy fatty acid amides, alkoxylated fatty acid esters, sucrose esters, amine oxides, and combinations thereof.

Zwitterionic surfactants suitable include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

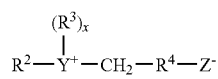

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical, wherein R is a $C_{11}$-$C_{17}$ alkyl, is attached to the nitrogen atom of the betaine are also useful in this invention.

Water-Soluble Polymer ("Polymer Structurant")

The Article comprises water-soluble polymer that functions as a structurant. As used herein, the term "water-soluble polymer" is broad enough to include both water-soluble and water-dispersible polymers, and is defined as a polymer with a solubility in water, measured at 25° C., of at least about 0.1 gram/liter (g/L). In some embodiments, the polymers have solubility in water, measured at 25° C., of from about 0.1 gram/liter (g/L) to about 500 grams/liter (g/L). (This indicates production of a macroscopically isotropic or transparent, colored or colorless solution). The polymers for making these solids may be of synthetic or natural origin and may be modified by means of chemical reactions. They may or may not be film-forming. These polymers should be physiologically acceptable, i.e., they should be compatible with the skin, mucous membranes, the hair and the scalp.

The one or more water-soluble polymers of the present invention are selected such that their weighted average molecular weight is from about 40,000 to about 500,000, in one embodiment from about 50,000 to about 400,000, in yet another embodiment from about 60,000 to about 300,000, and in still another embodiment from about 70,000 to about 200,000. The weighted average molecular weight is computed by summing the average molecular weights of each polymer raw material multiplied by their respective relative weight percentages by weight of the total weight of polymers present within the porous solid.

In one embodiment, at least one of the one or more water-soluble polymers is chosen such that a 2% by weight solution of the water-soluble polymer gives a viscosity at 20° C. of from about 4 centipoise to about 80 centipoise; in an alternate embodiment from about 5 centipoise to about 70 centipoise; and in another embodiment from about 6 centipoise to about 60 centipoise.

The water-soluble polymer may be present from about 10 wt % to about 50 wt % by weight of the Article of one or more water-soluble polymer, in one embodiment from about 15 wt % to about 40 wt %, and in a particular embodiment from about 20 wt % to about 30 wt % by weight of the Article of one or more water-soluble polymer.

The water-soluble polymer(s) of the present invention can include, but are not limited to, synthetic polymers including polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrollidone/vinyl acetate copolymers, copolymers of anionic, cationic and amphoteric monomers, and combinations thereof.

The water-soluble polymer(s) which are suitable may also be selected from naturally sourced polymers including those of plant origin examples of which include karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, and shellac.

Modified natural polymers are also useful as water-soluble polymer(s) in the present invention. Suitable modified natural polymers include, but are not limited to, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; and guar derivatives such as hydroxypropyl guar.

Preferred water-soluble polymers of the present invention include polyvinyl alcohols, polyvinylpyrrolidones, polyalkylene oxides, starch and starch derivatives, pullulan, gelatin, hydroxypropylmethylcelluloses, methycelluloses, and carboxymethycelluloses.

More preferred water-soluble polymers of the present invention include polyvinyl alcohols, and hydroxypropylmethylcelluloses. Suitable polyvinyl alcohols include those available from Celanese Corporation (Dallas, Tex.) under the CELVOL® trade name. Suitable hydroxypropylmethylcelluloses include those available from the Dow Chemical Company (Midland, Mich.) under the METHOCEL® trade name including combinations with above mentioned hydroxypropylmethylcelluloses.

In a particular embodiment, the above mentioned water-soluble polymer(s) may be blended with any single starch or combination of starches as a filler material in such an amount as to reduce the overall level of water-soluble polymers required, so long as it helps provide the Article with the requisite structure and physical/chemical characteristics as described herein.

In such instances, the combined weight percentage of the water-soluble polymer(s) and starch-based material generally ranges from about 10% to about 40 wt %, in one embodiment from about 12 to about 30%, and in a particular embodiment from about 15% to about 25% by weight relative to the total weight of the Article. The weight ratio of the water-soluble polymer(s) to the starch-based material can generally range from about 1:10 to about 10:1, in one embodiment from about 1:8 to about 8:1, in still another embodiment from about 1:7 to about 7:1, and in yet another embodiment from about 6:1 to about 1:6.

Typical sources for starch-based materials can include cereals, tubers, roots, legumes and fruits. Native sources can include corn, pea, potato, banana, barley, wheat, rice, sago, amaranth, tapioca, arrowroot, canna, sorghum, and waxy or high amylase varieties thereof.

The starch-based materials may also include native starches that are modified using any modification known in the art, including physically modified starches examples of which include sheared starches or thermally-inhibited starches; chemically modified starches including those which have been cross-linked, acetylated, and organically esterified, hydroxyethylated, and hydroxypropylated, phosphorylated, and inorganically esterified, cationic, anionic, nonionic, amphoteric and zwitterionic, and succinate and substituted succinate derivatives thereof, conversion products derived from any of the starches, including fluidity or thin-boiling starches prepared by oxidation, enzyme conversion, acid hydrolysis, heat or acid dextrinization, thermal and or sheared products may also be useful herein; and pregelatinized starches which are known in the art.

Plasticizer

The Article may comprise a water soluble plasticizing agent suitable for use in compositions discussed herein. Non-limiting examples of suitable plasticizing agents include polyols, copolyols, polycarboxylic acids, polyesters and dimethicone copolyols.

Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable platicizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

Preferred placticizers include glycerin and propylene glycol. EP 0283165 B1 discloses other suitable plasticizers, including glycerol derivatives such as propoxylated glycerol.

The plasticizer, may be present from 0 wt % to about 15 wt %, by weight of the Article of a plasticizer, alternatively from about 1 wt % to about 15 wt %, in one embodiment from about 3 wt % to about 12 wt %, and in another embodiment from about 5 wt % to about 10 wt % by weight of the Article of a plasticizer.

Optional Ingredients

The Article may further comprise other optional ingredients that are known for use or otherwise useful in personal care compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Non limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, vitamins, sunscreens, tanning agents, exfoliation particles, hair growth or restorer agents, insect repellents, having lotion agents, co-solvents or other additional solvents, and similar other materials.

Other preferred optional ingredients include organic solvents, especially water miscible solvents and co-solvents useful as solublizing agents for polymeric structurants and as drying accelerators. Non-limiting examples of suitable solvents include alcohols, esters, ketones, aromatic hydrocarbons, aliphatic hydrocarbons, ethers, and combinations thereof. Alcohols and esters are more preferred. Preferred alcohols are monohydric. The most preferred monohydric alcohols are ethanol, iso-propanol, and n-propanol. The most preferred esters are ethyl acetate and butyl acetate. Other non-limiting examples of suitable organic solvents are benzyl alcohol, amyl acetate, propyl acetate, acetone, heptane, isobutyl acetate, iso-propyl acetate, toluene, methyl acetate, iso-butanol, n-amyl alcohol, n-butyl alcohol, hexane, and methyl ethyl ketone methanol, ethanol, n-propanol, isopropanol, n-butanol, isobutanol, methylethylketone, acetone, and combinations thereof.

Other preferred optional ingredients include latex or emulsion polymers, thickeners such as water soluble polymers, clays, silicas, ethylene glycol distearate, deposition aids, including coacervate forming components and quaternary amine compounds.

Product Form

The Article can be produced in any of a variety of product forms, including dissolvable porous solids used alone or in combination with other personal care components. The dissolvable porous solids can be used in a continuous or discontinuous manner when used within personal care compositions. Regardless of the product form, the key to all of the product form embodiments contemplated within the scope of the method of the present invention is the selected and defined Article that comprises a combination of a solid polymeric structurant and a surfactant-containing active ingredient, all as defined herein.

The Article is preferably in the form of one or more flat sheets or pads of an adequate size to be able to be handled easily by the user. It may have a square, rectangle or disc shape or any other suitable shape. The pads can also be in the form of a continuous strip including delivered on a tape-like roll dispenser with individual portions dispensed via perforations and or a cutting mechanism. Alternatively, the Articles are in the form of one or more cylindrical objects, spherical objects, tubular objects or any other shaped object.

The Article may comprise one or more textured, dimpled or otherwise topographically patterned surfaces including letters, logos or figures. The textured substrate preferably results from the shape of the substrate, in that the outermost surface of the substrate contains portions that are raised with respect to other areas of the surface. The raised portions can result from the formed shape of the article, for example the article can be formed originally in a dimpled or waffle pattern. The raised portions can also be the result of creping processes, imprinted coatings, embossing patterns, laminating to other layers having raised portions, or the result of the physical form of the dissolvable porous solid substrate itself. The texturing can also be the result of laminating the substrate to a second substrate that is textured.

In a particular embodiment, the Article can be perforated with holes or channels penetrating into or through the porous solid. These perforations can be formed during the drying process via spikes extended from the surface of the underlying mold, belt or other non-stick surface. Alternatively, these perforations can be formed after the drying process via poking or sticking the porous solids with pins, needles or other sharp objects. Preferably, these perforations are great in number per surface area, but not so great in number so as to sacrifice the integrity or physical appearance of the porous solid. It has been found that such perforations increase the dissolution rate of the porous solids into water relative to un-perforated porous solids.

The Article can also be delivered via a water insoluble implement or device. For instance, they may be attached or glued by some mechanism to an applicator to facilitate application to hair and/or skin, i.e., a comb, rag, wand, or any other conceivable water-insoluble applicator. Additionally, the Article may be adsorbed to the surfaces a separate high surface area water-insoluble implement, i.e., a porous sponge, a puff, a flat sheet etc. For the latter, the dissolvable porous solid of the present invention may be adsorbed as a thin film or layer.

Product Types

Non-limiting examples of product type embodiments for use by the Article and methods of the present invention include hand cleansing substrates, hair shampoo or other hair treatment substrates, body cleansing substrates, shaving preparation substrates, pet care substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and so forth.

II. Method of Manufacture

The Article can be prepared by the process comprising: (1) Preparing a processing mixture comprising surfactant(s), dissolved polymer structurant, plasticizer and other optional ingredients; (2) Aerating the mixture by introducing a gas into the mixture; (3) Forming the aerated wet mixture into a desired one or more shapes; and (4) Drying the aerated wet mixture to a desired final moisture content (e.g., from about 0.5% to about 15% moisture, by addition of energy).

Preparation of Processing Mixture

The processing mixture is generally prepared by dissolving the polymer structurant in the presence of water, plasticizer and other optional ingredients by heating followed by cooling. This can be accomplished by any suitable heated batch agitation system or via any suitable continuous system involving either single screw or twin screw extrusion or heat exchangers together with either high shear or static mixing. Any process can be envisioned such that the polymer is ultimately dissolved in the presence of water, the surfactant(s), the plasticizer, and other optional ingredients including stepwise processing via pre-mix portions of any combination of ingredients.

The processing mixtures of the present invention comprise: from about 15% to about 40% solids, in one embodiment from about 20% to about 35% solids, and in another embodiment from about 25% to about 30% solids, by weight of the processing mixture before drying; and have a viscosity of from about 2,500 cps to about 30,000 cps, in one embodiment from about 5,000 cps to about 25,000 cps, in another embodiment from about 7,500 cps to about 20,000 cps, and in still another embodiment from about 10,000 cps to about 15,000 cps.

The % solids content is the summation of the weight percentages by weight of the total processing mixture of all of the solid, semi-solid and liquid components excluding water and any obviously volatile materials such as low boiling alcohols. The processing mixture viscosity values are measured using a TA Instruments AR500Rheometer with 4.0 cm diameter parallel plate and 1,200 micron gap at a shear rate of 1.0 reciprocal seconds for a period of 30 seconds at 23° C.

Aeration of Processing Mixture

The aeration of the processing mixture is accomplished by introducing a gas into the mixture, preferably by mechanical mixing energy but also may be achieved via chemical means. The aeration may be accomplished by any suitable mechanical processing means, including but not limited to: (i) Batch tank aeration via mechanical mixing including planetary mixers or other suitable mixing vessels, (ii) semi-continuous or continuous aerators utilized in the food industry (pressurized and non-pressurized), or (iii) spray-drying the processing mixture in order to form aerated beads or particles that can be compressed such as in a mould with heat in order to form the porous solid.

In a particular embodiment, it has been discovered that the Article can be prepared within continuous pressurized aerators that are conventionally utilized within the foods industry in the production of marshmallows. Suitable continuous pressurized aerators include the Morton whisk (Morton Machine Co., Motherwell, Scotland), the Oakes continuous automatic mixer (E. T. Oakes Corporation, Hauppauge, N.Y.), the Fedco Continuous Mixer (The Peerless Group, Sidney, Ohio), and the Preswhip (Hosokawa Micron Group, Osaka, Japan).

Forming the Aerated Wet Processing Mixture

The forming of the aerated wet processing mixture may be accomplished by any suitable means to form the mixture in a desired shape or shapes including, but not limited to (i) depositing the aerated mixture to moulds of the desired shape and size comprising a non-interacting and non-stick surface including aluminium, Teflon, metal, HDPE, polycarbonate, neoprene, rubber, LDPE, glass and the like; (ii) depositing the aerated mixture into cavities imprinted in dry granular starch contained in a shallow tray, otherwise known as starch moulding forming technique; and (iii) depositing the aerated mixture onto a continuous belt or screen comprising any non-interacting or non-stick material Teflon, metal, HDPE, polycarbonate, neoprene, rubber, LDPE, glass and the like which may be later stamped, cut, embossed or stored on a roll.

Drying the Formed Aerated Wet Processing Mixture

The drying of the formed aerated wet processing mixture may be accomplished by any suitable means including, but not limited to (i) drying room(s) including rooms with controlled temperature and pressure or atmospheric conditions; (ii) ovens including non-convection or convection ovens with controlled temperature and optionally humidity; (iii) Truck/Tray driers, (iv) multi-stage inline driers; (v) impingement ovens; (vi) rotary ovens/driers; (vii) inline roasters; (viii) rapid high heat transfer ovens and driers; (ix) dual plenum roasters, and (x) conveyor driers.

Optional ingredients may be imparted during any of the above described four processing steps or even after the drying process.

The Article may also be prepared with chemical foaming agents by in-situ gas formation (via chemical reaction of one or more ingredients, including formation of $CO_2$ by an effervescent system).

III. Physical Characteristics

Dissolution Rate

The Article has a Dissolution Rate that allows the porous solid to rapidly disintegrate during use application with water. The Dissolution Rate of the Article is determined in accordance with the two methodologies described below.

Conductivity Dissolution Method: In a 250 ml beaker, 150+/−0.5 grams of distilled water is weighed at room temperature. The beaker is placed on an orbital shaker, for example a VWR model DS-500E and started at 150 RPM. A conductivity probe, for example a VWR model 2052 connected to a VWR conductivity meter, is submerged just below the surface of the water in such a manner that the conductivity probe remains stationary in relation to the motion of the beaker and never touches the side of the beaker. A 0.20+/−0.01 grams of the dissolvable porous solid is weighed and placed into the water. Conductivity data is recorded every 15 seconds for 6 minutes, and then once a minute until 30 minutes. The final value is recorded when the conductivity values stopped changing or 30 minutes is reached, whichever is earlier. The conductivity dissolution time is taken as the time it takes in seconds until the conductivity values stop changing or as the maximum of 30 minutes, which ever happens first.

The Article has a conductivity dissolution time of from about 100 seconds to about 1,200 seconds, in another embodiment from about 110 seconds to about 900 seconds, in yet another embodiment from about 120 seconds to about 600 seconds, and in still another embodiment from about 130 seconds to about 300 seconds.

Hand Dissolution Method: 0.5 g of the dissolvable porous solid is placed in the palm of the hand while wearing nitrile gloves. 7.5 cm$^3$ of luke warm tap water (from about 30° C. to about 35° C.) is quickly applied to the product via syringe. Using a circular motion, palms of hands are rubbed together 2 strokes at a time until dissolution occurs (up to 30 strokes). Undissolved material (after 30 strokes) is placed in pre-weighed weigh boat. Dry weight of undissolved material is measure the following day. The hand dissolution value is reported as the number of strokes it takes for complete dissolution or as 30 strokes as the maximum. For the latter scenario, the weight of the undissolved material is also reported.

The Article has a hand dissolution value of from about 1 to about 30 strokes, in one embodiment from about 2 to about 25 strokes, in another embodiment from about 3 to about 20 strokes, and in still another embodiment from about 4 to about 15 strokes.

Lather Volume

The Article provides a lather profile as described hereafter. The lather volume assessment is performed on 15 g/10 inch flat Oriental virgin hair switches that have been treated with 0.098 g of artificial liquid sebum [10-22% olive oil, 18-20% coconut oil, 18-20% oleic acid, 5-9% lanolin, 5-9% squalene, 3-6% palmitic acid, 3-6% paraffin oil, 3-6% dodecane, 1-4% stearic acid, 1-4% cholesterol, 1-4% coconut fatty acid, 18-20% choleth-24]. The hair switch is rinsed with 9-11 grain, 100° F. water at 1.5 gallons/min for 20 seconds with a shower nozzle. For testing the liquid control products, 0.75 cm$^3$ of liquid product are applied to the center of the switch, the lower portion of hair on the switch is then rubbed over the product on the hair 10 times in a circular motion, followed by 40 strokes back and forth (a total of 80 strokes). Lather speed is recorded as the number of strokes when the first lather is obviously generated during the 80 strokes. Lather from operator's gloves is transferred to a graduated cylinder with a 3.5 cm inside diameter and with total capacities of either 70 ml, 110 ml, or 140 ml depending on the total amount of lather generated (height modification of standard sized graduated cylinders via a glass shop). Lather from hair is gathered using one downward stroke on the switch with a tight grip and is also placed into the cylinder. Total lather volume is recorded in milliliters. Three runs per test sample are performed and the mean of the three values is calculated. When testing the Article, 0.20+/−0.01 grams of product are weighed with the aid of scissors if required and applied to the switch and then 2 cm$^3$ of additional water are added to the product via syringe. The lathering technique is then performed as described for liquid products after a 10 second waiting time.

Lamellar Liquid Crystals

The presence of lamellar liquid crystals within the processing mixture can be assessed by simple microscopic observation under cross polarizers. The sample is pressed out between a slide and coverglass. The presence of lamellar liquid crystals can be assessed by the visual observation of birefringence in the form of various textures characteristic of liquid crystalline neat phases as can be referenced [Rosevear, F. B., "The Microscopy of the Liquid Crystalline Neat and Middle Phase of Soaps and Synthetic Detergents", The Journal of the Americal Oil Chemists' Society, December 1954 Issue, Vol. XXXI, No. 12. Pages 628-639].

Distance to Maximum Force Method

The distance to maximum force is measured via a Rupture Method on a Texture Analyzer using a TA-57R cylindrical probe with Texture Exponent 32 Software. The Article should have a thickness of between 4 to 7 mm and cut in a circle with a diameter of at least 7 mm for this method; or carefully cut or stacked to be within this overall thickness and diameter range. The porous solid sample is carefully mounted on top of the cylinder with four screws mounted on top with the top lid affixed in place on top of the sample. There is a hole in the center of the cylinder and its lid which allows the probe to pass through and stretch the sample. The sample is measured with a pre-test speed of 1 mm per second, a test speed of 2 mm per second and a post test speed of 3 mm per second over a total distance of 30 mm. The distance to maximum force is recorded.

IV. Methods of Use

The compositions of the present invention may be used for cleansing and otherwise treating mammalian keratinous tissue such as hair and/or skin, and provide rapid lathering and/or rinse-ability. The method for cleansing and conditioning the hair may comprise the steps of: a) applying an effective amount of the dissolvable porous solid to the hand, b) wetting the dissolvable porous solid with water and rubbing to dissolve the solid, c) applying the dissolved material to either the hair or skin such as to treat or cleanse, and d) rinsing the diluted treatment or cleansing composition from the hair or skin using water. These steps can be repeated as many times as desired to achieve the desired cleansing and or treatment benefit.

According to yet another embodiment, a method is provided for providing a benefit to mammalian keratinous tissue, comprising the step of applying a composition according to the first embodiment to keratinous tissue in need of regulating.

The present invention provides for a method for regulating the condition of mammalian keratinous tissue, comprising the step of applying one or more compositions described herein to mammalian keratinous tissue in need of regulation.

The amount of the composition applied, the frequency of application and the period of use will vary widely depending upon the purpose of application, the level of components of a given composition and the level of regulation desired. For example, when the composition is applied for whole body or hair treatment, effective amounts generally range from about 0.3 grams to about 10 grams, preferably from about 0.4 grams to about 5 grams, and more preferably from about 0.5 grams to about 3 grams.

V. Article of Commerce

The present invention provides for an article of commerce comprising one or more compositions described herein, and a communication directing a consumer to dissolve the porous solid and apply the dissolved mixture to keratinous tissue to produce a cleansing effect, a benefit to keratinous tissue such as skin and/or hair, a rapidly lathering foam, a rapidly rinsing foam, a clean rinsing foam, and combinations thereof. The communication may be printed material attached directly or indirectly to packaging that contains the composition or on the composition itself. Alternatively, the communication may be an electronic or a broadcast message that is associated with the article of manufacture. Alternatively, the communication may describe at least one possible use, capability, distinguishing feature and/or property of the article of manufacture.

VI. EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Example 1

Dissolving Porous Solid Cleanser with Polyvinyl Alcohol

The following dissolving porous solid is prepared in accordance to the present invention:

TABLE 1

| Component | Wt % |
| --- | --- |
| Distilled water | 23.4 |
| Glycerin | 2.9 |
| Polyvinyl alcohol[1] | 7.3 |
| Ammonium Laureth-3 sulfate (25% activity) | 40.0 |
| Ammonium Lauryl sulfate (25% activity) | 24.0 |
| Cetyl alcohol | 0.9 |
| Cocamide MEA | 1.5 |
| Total | 100.0 |

[1]CELVOL ® 523 available from Celanese Corporation (Dallas, Texas)

Into an appropriately sized and cleaned vessel, the distilled water and glycerin is added with stirring at 100-300 rpm. The CELVOL® 523 is weighed into a suitable container and slowly added to the main mixture in small increments using a spatula while continuing to stir while avoiding the formation of visible lumps. The mixing speed is adjusted to minimize foam formation. The mixture is slowly heated to 75° C. after which the ammonium laureth-3 sulfate and ammonium lauryl sulfate are added. The mixture is allowed to again reach 75° C. and the cetyl alcohol and cocamide MEA is added. The mixture is then heated to 85° C. while continuing to stir and then allowed to cool to room temperature. The final pH is between 5.2-6.6 and adjusted with citric acid or diluted sodium hydroxide if necessary. The viscosity of the mixture is approximately 12,000 to 15,000 cps at 1 $s^{-1}$. The mixture was analyzed under an optical light microscope between cross-polarizers and determined to comprise lamellar liquid crystals based on significant birefringence.

250 grams of the above mixture is transferred into a 5 quart stainless steel bowl of a KITCHENAID® Mixer Model K5SS (available from Hobart Corporation, Troy, Ohio) and fitted with a flat beater attachment. The mixture is vigorously aerated at high speed for 30 seconds. A portion of the resulting aerated mixture is then spread with a spatula into 12 circular Teflon molds with a 4.2 cm diameter and a depth of 0.6 cm which are weighed indicating an average wet foam density of approximately 0.31 grams/$cm^3$. The remaining mixture is aerated again for an additional 30 seconds for a total of 60 seconds. A portion of the resulting aerated mixture is then spread with a spatula into 12 circular Teflon molds with a 4.2 cm diameter and a depth of 0.6 cm which are weighed indicating an average wet foam density of approximately 0.21 grams/$cm^3$. The remaining mixture is aerated again for an additional 30 seconds for a total of 90 seconds. A portion of the resulting aerated mixture is then spread with a spatula into 12 circular Teflon molds with a 4.2 cm diameter and a depth of 0.6 cm which are weighed indicating an average wet foam density of approximately 0.19 grams/$cm^3$.

The segregated molds are then placed into a 75° C. convection oven for 30 minutes and then placed into a 40° C. convection oven for drying overnight. The following day, the resulting porous solids are removed from the molds with the aid of a thin spatula and tweezers. The molds were weighed indicating approximate average dry densities of 0.09 grams/$cm^3$ (540 grams per square meter basis weight), 0.07 grams/$cm^3$ (420 grams per square meter basis weight), and 0.06 grams/$cm^3$ (360 grams per square meter basis weight) for the 30 second, 60 second and 90 second mix times, respectively. The estimated surfactant levels are between 48 wt % and 64 wt % and the estimated polymer level is between 19% and 26%, assuming a moisture content of between 0 wt % and 10 wt %. The lather volumes for the 30 second, 60 second and 90 second mix times were 75 ml, 80 ml and 65 ml, respectively.

Comparative Example 2

Non-Dissolving Porous Cleanser Solid with Hydroxypropylmethyl Cellulose

The following dissolving porous solid is not prepared in accordance to the present invention and is included only for comparative purposes:

TABLE 2

| Component | Wt % |
| --- | --- |
| Distilled water | 24.3 |
| Glycerin | 2.0 |
| Hydroxypropylmethyl cellulose[1] | 7.3 |
| Ammonium Laureth-3 sulfate (25% activity) | 40.0 |
| Ammonium Lauryl sulfate (25% activity) | 24.0 |
| Cetyl alcohol | 0.9 |
| Cocamide MEA | 1.5 |
| Total | 100.0 |

[1]METHOCEL ® E50 available from Dow Chemical Corporation (Midland, Michigan)

Into an appropriately sized and cleaned vessel, the distilled water and glycerin is added with stirring at 100-300 rpm. The METHOCEL® E50 is weighed into a suitable container and slowly added to the main mixture in small increments using a spatula while continuing to stir while avoiding the formation of visible lumps. The mixing speed is adjusted to minimize foam formation. The mixture is slowly heated to 75° C. after which the ammonium laureth-3 sulfate and ammonium lauryl sulfate are added. The mixture is allowed to again reach 75° C. and the cetyl alcohol and cocamide MEA is added. The mixture is then heated to 85° C. while continuing to stir and then allowed to cool to room temperature. The final pH is between 5.2-6.6 and adjusted with citric acid or diluted sodium hydroxide if necessary. The viscosity of the mixture is approximately 55,000 to 65,000 cps at 1 $s^{-1}$. The mixture was analyzed under an optical light microscope between cross-polarizers and determined to be isotropic based on the absence of observable birefringence.

The same aeration and drying procedure is performed as described in Example 1 giving approximate average wet and dry densities as indicated in Table 3. The estimated surfactant levels are between 49 wt % and 66 wt % and the estimated polymer level is between 19 wt % and 26 wt %, assuming a moisture content of between 0 wt % and 10 wt %.

TABLE 3

|  | 30 seconds mixing | 60 seconds mixing | 90 seconds mixing |
|---|---|---|---|
| Wet Density | 0.64 grams/cm$^3$ | 0.54 grams/cm$^3$ | 0.55 grams/cm$^3$ |
| Dry Density | 0.21 grams/cm$^3$ | 0.17 grams/cm$^3$ | 0.17 grams/cm$^3$ |
| Dry Basis Weight | 1,260 grams/m$^2$ | 1,020 grams/m$^2$ | 1,020 grams/m$^2$ |
| Lather Volume | 55 ml | 60 ml | 70 ml |

Example 3

Dissolving Porous Solid Cleanser with Hydroxypropylmethyl Cellulose

The following dissolving porous solid is prepared in accordance to the present invention. 80 parts of the identical composition of example 2 with hydropropylmethyl cellulose is diluted with 20 parts distilled water. The viscosity of the mixture is approximately 12,000 to 15,000 cps at 1 s$^{-1}$. The mixture was analyzed under an optical light microscope between cross-polarizers and determined to be isotropic based on the absence of observable birefringence.

The same aeration and drying procedure is performed as described in Example 1 giving approximate average wet and dry densities as indicated in Table 4. The estimated surfactant levels are between 49 wt % and 66 wt % and the estimated polymer level is between 19 wt % and 26 wt %, assuming a moisture content of between 0 wt % and 10 wt %.

TABLE 4

|  | 30 seconds mixing | 60 seconds mixing | 90 seconds mixing |
|---|---|---|---|
| Wet Density | 0.43 grams/cm$^3$ | 0.29 grams/cm$^3$ | 0.27 grams/cm$^3$ |
| Dry Density | 0.10 grams/cm$^3$ | 0.07 grams/cm$^3$ | 0.07 grams/cm$^3$ |
| Dry Basis Weight | 600 grams/m$^2$ | 420 grams/m$^2$ | 420 grams/m$^2$ |
| Lather Volume | 65 ml | 65 ml | 85 ml |

Comparative Example 4

Non-dissolving Porous Cleanser Solid with Polyvinyl Alcohol

The following dissolving porous solid is not prepared in accordance with the present invention and is included only for comparative purposes:

TABLE 5

| Component | Wt % |
|---|---|
| Distilled water | QS 100 |
| Glycerin | 1.0 |
| Polyvinyl alcohol[1] | 7.3 |
| Sodium Laureth-3 sulfate (28% activity) | 35.7 |
| Sodium Lauryl sulfate (29% activity) | 20.7 |
| Cetyl alcohol | 0.9 |
| Cocamide MEA | 1.5 |
| Tetrasodium EDTA | 0.04 |
| Sodium benzoate | 0.08 |
| Kathon CG[2] | 0.01 |

[1]CELVOL ® 523 available from Celanese Corporation (Dallas, Texas)
[2]5-chloro-2-methyl-4-isothiazolin-3-one and 2-methyl-4-isothiazoliin-3-one available from Rohm and Haas (Philadelphia, PA).

Into an appropriately sized and cleaned vessel, the distilled water and glycerin is added with stirring at 100-300 rpm. The CELVOL® 523 is weighed into a suitable container and slowly added to the main mixture in small increments using a spatula while continuing to stir while avoiding the formation of visible lumps. The mixing speed is adjusted to minimize foam formation. The mixture is slowly heated to 75° C. after which the sodium laureth-3 sulfate and sodium lauryl sulfate are added. The mixture is allowed to again reach 75° C. and the cetyl alcohol and cocamide MEA is added. The mixture is then heated to 85° C. while continuing to stir and then allowed to cool to room temperature. The final pH is between 5.2-6.6 and adjusted with citric acid or diluted sodium hydroxide if necessary. The viscosity of the mixture is approximately 65,000 to 75,000 cps at 1 s$^{-1}$.

The same aeration and drying procedure is performed as described in Example 1 giving approximate average wet and dry densities as indicated in Table 6. The estimated surfactant levels are between 50 wt % and 69 wt % and the estimated polymer level is between 20% and 27%, assuming a moisture content of between 0 wt % and 10 wt %.

TABLE 6

|  | 30 seconds mixing | 60 seconds mixing | 90 seconds mixing |
|---|---|---|---|
| Wet Density | 0.61 grams/cm$^3$ | 0.49 grams/cm$^3$ | 0.42 grams/cm$^3$ |
| Dry Density | 0.21 grams/cm$^3$ | 0.16 grams/cm$^3$ | 0.13 grams/cm$^3$ |
| Dry Basis Weight | 1,260 grams/m$^2$ | 960 grams/m$^2$ | 780 grams/m$^2$ |
| Lather Volume | 40 ml | 45 ml | 50 ml |

Example 5

Dissolving Porous Cleanser Solid with Polyvinyl Alcohol and Hydrotrope

The following dissolving porous solid is prepared in accordance to the present invention:

TABLE 7

| Component | Wt % |
| --- | --- |
| Distilled water | QS 100 |
| Glycerin | 1.0 |
| Polyvinyl alcohol[1] | 7.3 |
| Sodium Laureth-3 sulfate (28% activity) | 35.7 |
| Sodium Lauryl sulfate (29% activity) | 20.7 |
| Cetyl alcohol | 0.9 |
| Cocamide MEA | 1.5 |
| Tetrasodium EDTA | 0.04 |
| Sodium benzoate | 0.08 |
| Kathon CG[2] | 0.01 |
| Sodium xylene sulfonate (40.5% active) | 11.1 |

[1]CELVOL ® 523 available from Celanese Corporation (Dallas, Texas)
[2]5-chloro-2-methyl-4-isothiazolin-3-one and 2-methyl-4-isothiazoliin-3-one available from Rohm and Haas (Philadelphia, PA).

Into an appropriately sized and cleaned vessel, the distilled water and glycerin is added with stirring at 100-300 rpm. The CELVOL® 523 is weighed into a suitable container and slowly added to the main mixture in small increments using a spatula while continuing to stir while avoiding the formation of visible lumps. The mixing speed is adjusted to minimize foam formation. The mixture is slowly heated to 75° C. after which the sodium laureth-3 sulfate and sodium lauryl sulfate are added. The mixture is allowed to again reach 75° C. and the cetyl alcohol and cocamide MEA is added. The mixture is then heated to 85° C. while continuing to stir and then allowed to cool to room temperature. Sodium xylene sulfonate is added to reduce the viscosity of the mixture. The final pH is between 5.2-6.6 and adjusted with citric acid or diluted sodium hydroxide if necessary. The viscosity of the mixture is approximately 12,000 to 15,000 cps at $1\ s^{-1}$.

The same aeration and drying procedure is performed as described in Example 1 giving approximate average wet and dry densities as indicated in Table 8. The estimated surfactant levels are between 45 wt % and 59 wt % and the estimated polymer level is between 18% and 23%, assuming a moisture content of between 0 wt % and 10 wt %.

TABLE 8

| | 30 seconds mixing | 60 seconds mixing | 90 seconds mixing |
| --- | --- | --- | --- |
| Wet Density | 0.34 grams/cm$^3$ | 0.23 grams/cm$^3$ | 0.18 grams/cm$^3$ |
| Dry Density | 0.12 grams/cm$^3$ | 0.08 grams/cm$^3$ | 0.07 grams/cm$^3$ |
| Dry Basis Weight | 720 grams/m$^2$ | 480 grams/m$^2$ | 420 grams/m$^2$ |
| Lather Volume | 50 ml | 60 ml | 55 ml |

Examples 6-18

Porous Solid Structural and Dissolution Performance Data

Table 9 summarizes the dissolution rate data (conductivity method and hand method) and cell inter-connectivity data (structure model index and star volume index) taken on the prepared dissolvable and comparative non-dissolvable porous solids as described in examples 1 through 6. The data was collected by the methods as described herein. Representative visual images of the porous solids can be found in FIGS. 1 through 14.

TABLE 9

Figure 2:
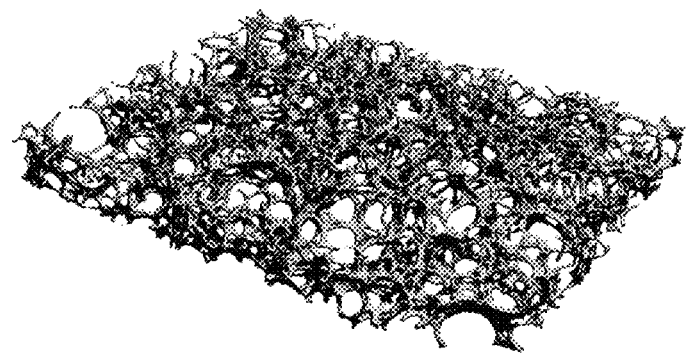
FIG. 2 is a micro computed tomography system image of Example 1 as discussed in Table 9
Figure 3:
FIG. 3 is a micro computed tomography system image of Example 1 as discussed in Table 9
Figure 4:
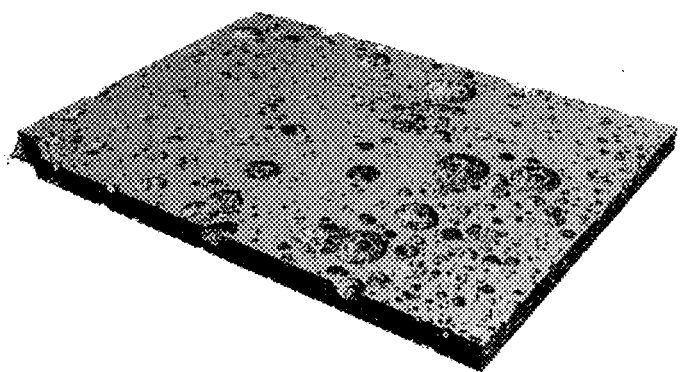
FIG. 4 is a micro computed tomography system image of Example 2 as discussed in Table 9
Figure 5:
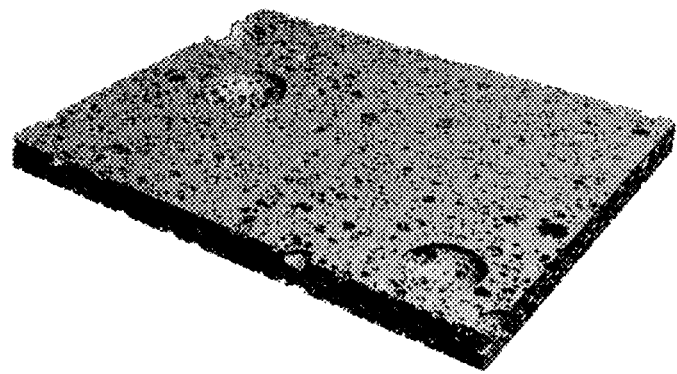
FIG. 5 is a micro computed tomography system image of Example 2 as discussed in Table 9
Figure 6:
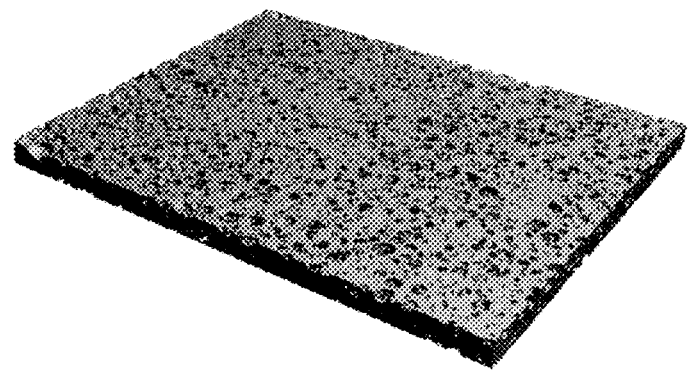
FIG. 6 is a micro computed tomography system image of Example 2 as discussed in Table 9
Figure 7:
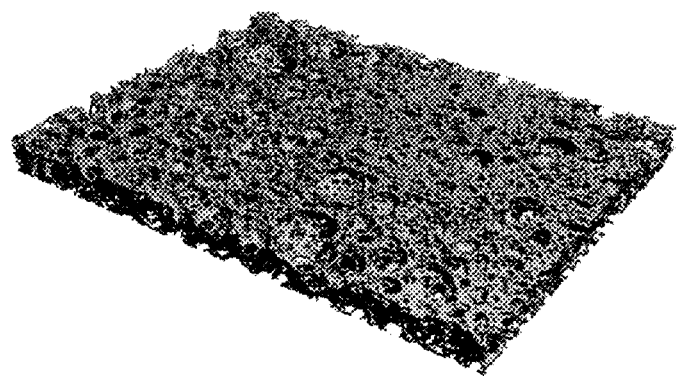
FIG. 7 is a micro computed tomography system image of Example 3 as discussed in Table 9
Figure 8:
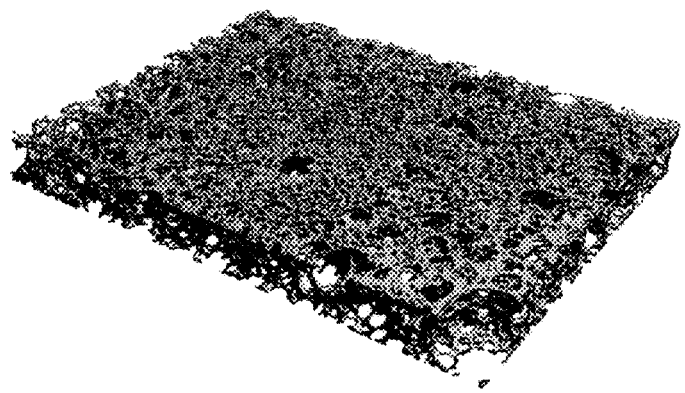
FIG. 8 is a micro computed tomography system image of Example 3 as discussed in Table 9
Figure 9:
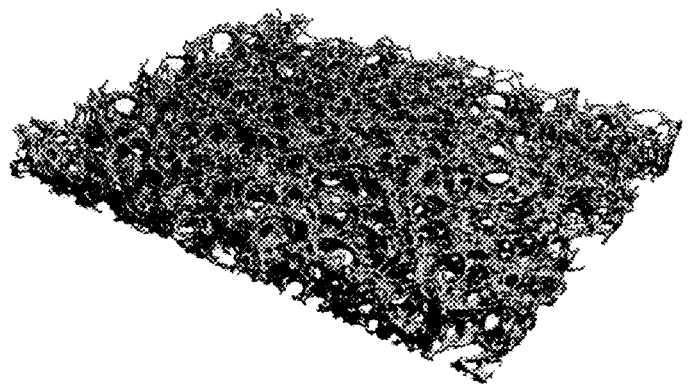
FIG. 9 is a micro computed tomography system image of Example 3 as discussed in Table 9
Figure 10:
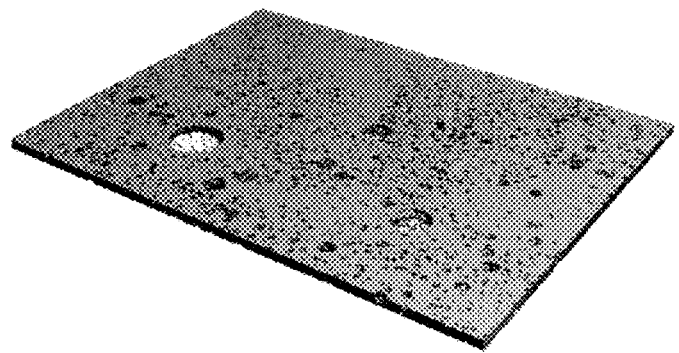
FIG. 10 is a micro computed tomography system image of Example 4 as discussed in Table 9
Figure 11:
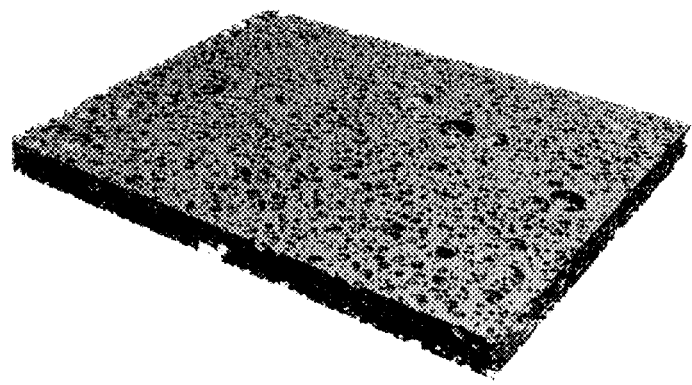
FIG. 11 is a micro computed tomography system image of Example 4 as discussed in Table 9
Figure 12:
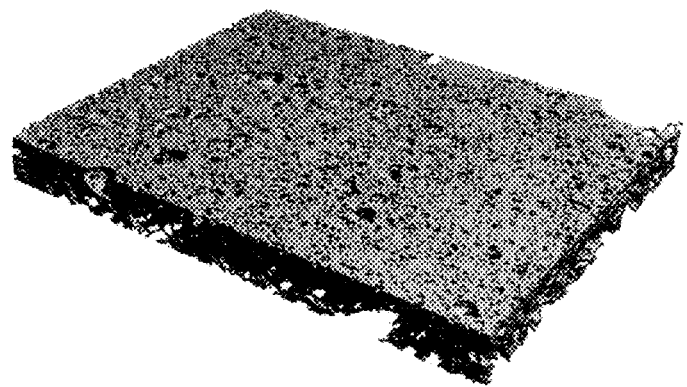
FIG. 12 is a micro computed tomography system image of Example 5 as discussed in Table 9
Figure 13:
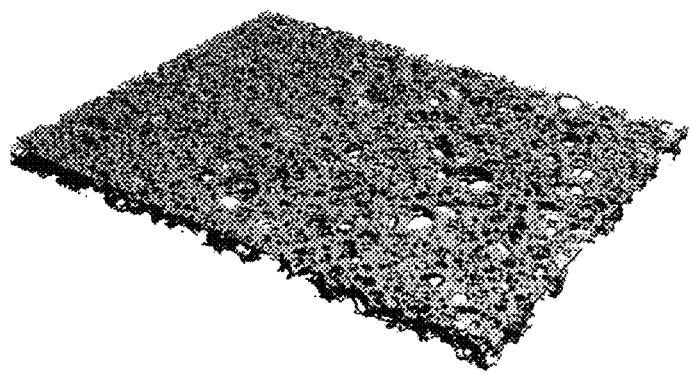
FIG. 13 is a micro computed tomography system image of Example 5 as discussed in Table 9

| | Porous Solid Description | Mix Time | Dissolution Rate | | Cell Inter-connectivity | | Image Ref. |
| --- | --- | --- | --- | --- | --- | --- | --- |
| | | | Conductivity Method | Hand Method[1] | Structure Model Index | Star Volume | |
| 6 | Dissolving Porous Solid Cleanser with polyvinyl alcohol (Ex. 1) | 30 s | 480 s | 30 (0.02 g) | 1.8 | 19.8 mm$^3$ | FIG. 1 |
| 7 | | 60 s | 220 s | 16 | 2.0 | 53.8 mm$^3$ | FIG. 2 |
| 8 | | 90 s | 250 s | 9 | 2.3 | 43.7 mm$^3$ | FIG. 3 |
| 9 | Non-dissolving Porous Cleanser Solid with hydroxypropylmethyl cellulose (Comparative Ex 2) | 30 s | >1800 s | 30 (0.33 g) | −3.5 | 0.2 mm$^3$ | FIG. 4 |
| 10 | | 60 s | >1800 s | 30 (0.24 g) | −1.6 | 0.8 mm$^3$ | FIG. 5 |
| 11 | | 90 s | >1800 s | 30 (0.27 g) | −1.0 | 0.1 mm$^3$ | FIG. 6 |
| 12 | Dissolving Porous Solid Cleanser with hydroxypropylmethyl cellulose (Ex 3) | 30 s | 840 s | 30 (0.16 g) | 1.0 | 2.4 mm$^3$ | FIG. 7 |
| 13 | | 60 s | 660 s | 19 | 1.5 | 10.4 mm$^3$ | FIG. 8 |
| 14 | | 90 s | 450 s | 11 | 1.6 | 23.5 mm$^3$ | FIG. 9 |
| 15 | Non-dissolving Porous Cleanser Solid with polyvinyl alcohol (Comparative Ex 4) | 30 s | >1800 s | 30 (0.34) | −5.0 | 0.0 mm$^3$ | FIG. 10 |
| 16 | | 60 s | 660 s | 30 (0.26) | −0.7 | 0.4 mm$^3$ | FIG. 11 |
| 17 | Dissolving Porous Solid with PVOH and hydrotrope (Ex 5) | 30 s | 165 s | 30 (0.06) | 0.02 | 3.4 mm$^3$ | FIG. 12 |
| 18 | | 60 s | 180 s | 19 | 1.1 | 2.4 mm$^3$ | FIG. 13 |

[1]Amount in grams of undissolved material after maximum of 30 strokes presented in parentheses.

Example 19

Dissolving Porous Shave Preparation Gel With Polyvinyl Alcohol

The following dissolving porous solid is prepared in accordance to the present invention:

TABLE 10

| Component | Wt % |
|---|---|
| Distilled water | 64.9 |
| Triethanolamine | 5.9 |
| Polyvinyl alcohol[1] | 4.6 |
| Myristic acid | 4.9 |
| Sodium lauroyl sarcosinate[2] | 3.5 |
| Laureth-23 (Brij-35) | 2.5 |
| Palmitic acid | 2.4 |
| Oleth-20 | 2.1 |
| Glycerin | 1.4 |
| Sorbitol (70%) | 1.1 |
| Hydroxyethylcellulose[3] | 1.0 |
| PEG-150 Distearate | 0.7 |
| Glydant (DMDM Hydantoin) | 0.14 |
| Tetrasodium EDTA | 0.04 |
| Carbopol Aqua CC | 3.5 |
| Poly(ethylene oxide)[4] | 1.3 |
| Total | 100.0 |

[1]Aldrich, MW 85,000-124,000, 87-89% hydrolyzed
[2]Hamposyl L-30 (Hampshire Chemical, New Hampshire)
[3]Natrosol 250 HHR (Aqualon, New Jersey)
[4]Alkox E30-G (Tri-tex, Canada)

Into an appropriately sized and cleaned vessel, the distilled water is added with stirring at 100-300 rpm. The hydroxyethylcellulose is weighed into a suitable container and slowly added to the main mixture in small increments using a spatula while continuing to stir while avoiding the formation of visible lumps. The mixing speed is adjusted to minimize foam formation. The mixture is slowly heated to 65C after which the myristic acid, PEG-150 Distearate, Oleth-20, laureth-23, and palmitic acid are added. The mixture is then heated to 75° C. and the TEA is added. The mixture is then mixed for 30 minutes and allowed to cool to 45° C. after which the sodium lauroyl sarcosinate, tetrasodium EDTA, glycerin and sorbitol are added. The mixture is then cooled to 35° C. after which the Glydant is added. The mixture is then transferred to a container and stored in an oven along-side the poly(vinyl alcohol) at 70-75° C. for 30 minutes. The mixture is then placed in a water bath kept at 70-75° C. and mixed with an overhead stirrer at 275 rpm with the poly(vinyl alcohol) added slowly and then mixed for an additional 3 minutes. The Carbopol Aqua CC is then added slowly drop-wise along with the slow addition of the poly(ethylene oxide) followed by mixing for 2 minutes until complete dissolution.

The above heated mixture is then transferred into a 5 quart stainless steel bowl of a KITCHENAID® Mixer Model K5SS (available from Hobart Corporation, Troy, Ohio) and fitted with a flat beater attachment. The mixture is vigorously aerated at high speed for 3 minutes. The aerated mixture is then spread with a spatula into circular Teflon molds with a 4.2 cm diameter and a depth of 0.6 cm.

The segregated molds are then placed into a 75° C. convection oven for 60 minutes and then placed into a 40° C. convection oven for drying overnight. The following day, the resulting porous solids are removed from the molds with the aid of a thin spatula and tweezers and then placed in labeled bags. The resulting dissolvable porous solids exhibit rapid dissolution in the hands and easily work up into a thick, rich lather to facilitate the shaving of skin.

Example 20-23

Representative Porous Solid Structural Measurements

The following structural measurements were made of the porous solid produced in from processing mixture Examples 1 through 3 and with mix times of 90 seconds corresponding to Examples 8, 11 and 14. The structural measurements were made in accordance with the methods as described herein.

TABLE 11

Structural Characterization

| Example | Porous Solid Description | Mix Time | Kr BET Surface Area (m²/g) | Pycnometry % Open Cells | Micro-CT Cell Wall thickness (mm) |
|---|---|---|---|---|---|
| Ex. 20 | Dissolving Porous Solid Cleanser with polyvinyl alcohol (Ex. 1 & Ex. 8) | 90 s | 0.056 | 96.5% | 0.112 |
| Ex. 21 | Non-dissolving Porous Cleanser Solid with hydroxypropylmethyl cellulose (Comparative Ex. 2 & Ex. 11) | 90 s | 0.026 | 79.8% | 0.156 |
| Ex. 22 | Dissolving Porous Solid Cleanser with hydroxypropylmethyl cellulose (Ex 3 & Ex. 14) | 90 s | 0.063 | 94.1% | 0.116 |

Discussion of Examples

As can be seen in the tabulated figures for Examples 6 through 19, appreciable dissolution does not occur below a Star Volume of approximately 1 mm³ and a structure model index below zero. Above these limits, the dissolution rates are positively correlated to the magnitude of these two parameters. While not being bound to theory, it is believed that this data is indicative of a minimum degree of cell inter-connectivity being required for appreciable dissolution under the time frames of the methods. Below this minimum degree, the porous solids can be characterized as having a significant degree of closed-cells as is supported by the negative structure model indices indicating significant concavity among the cells. As can be seen from the table, comparative examples 2 and 4 comprised too low a degree of cell interconnectivity with corresponding slower dissolution rates than what is required for the present invention. Visual image representations of the porous solids can be inspected in FIGS. 1 through 14 as given herein.

The above data in Examples 6 through 19 also demonstrate single-variably the processing mixture viscosity range of the present invention produces rapidly dissolving open-celled porous solids independently of polymer type and surfactant system type as is demonstrated single-variably.

Examples 6 through 8 were produced from a processing mixture (Example 1) comprising polyvinyl alcohol and ammonium based sulfonated surfactant system and with viscosity of between 12,000 to 15,000 cps at 1 s$^{-1}$ in accord with the present invention.

Accordingly, Examples 6 through 8 produced predominantly open-celled porous solids as indicated by the high Star Volume values and positive Structure Model Index values with correspondingly rapid dissolution rates as measured by both conductivity and the hand methods.

Examples 9 through 11 were produced from a processing mixture (Example 2) with the identical ammonium based sulfonated surfactant system but with hydroxypropylmethyl cellulose substituted single-variably in place of the polyvinyl alcohol and with a resulting viscosity of between 55,000 to 65,000 cps at 1 s$^{-1}$ which is not in accord with the present invention.

Accordingly Examples 9 through 11 produced predominantly closed-celled porous solids as indicated by the low Star Volume values below 1.0 and the negative Structure Model Index values with correspondingly slow dissolution rates as measured by both the conductivity and the hand methods.

Examples 12 through 14 were produced from a processing mixture (Example 3) that was formed by diluting the identical composition as examples 9 through 11 as 80 parts with 20 parts de-ionized water in single-variable fashion with a resulting lower viscosity of between 12,000 to 15,000 cps at 1 s$^{-1}$ which is in accord with the present invention.

Accordingly, Examples 12 through 14 produced predominantly open-celled porous solids as indicated by the high Star Volume values and positive Structure Model Index values with correspondingly rapid dissolution rates as measured by both conductivity and the hand methods.

Examples 15 and 16 were produced from a processing mixture (Example 4) with the identical composition as examples 6 through 8 comprising polyvinyl alcohol but with sodium based alkyl sulfate surfactants substituted single-variably in place of the ammonium based alkyl sulfate surfactants and with a resulting viscosity of between 65,000 to 75,000 cps at 1 s$^{-1}$ which is not in accord with the present invention.

Accordingly Examples 15 and 16 produced predominantly closed-celled porous solids as indicated by the low Star Volume values below 1.0 and the negative Structure Model Index values with correspondingly slower dissolution rates as measured by both the conductivity and the hand methods.

Examples 17 and 18 were produced from a processing mixture (Example 5) with the identical composition as examples 15 and 16 comprising polyvinyl alcohol and sodium based alkyl sulfate surfactants but with a hydrotrope added single-variably and with a resulting viscosity of between 12,000 to 15,000 cps at 1 s$^{-1}$ which is in accord with the present invention.

Accordingly Examples 17 and 18 produced predominantly open-celled porous solids as indicated by the higher Star Volume values above 1.0 and the positive Structure Model Index values with correspondingly faster dissolution rates as measured by both the conductivity and the hand methods.

The above demonstrated discovery that rapidly dissolving porous solids according to the present invention can be produced independently of polymer type and surfactant system type is surprising and goes against the conventionally accepted wisdom that is the polymer type, and specifically the molecular weight, that is the primary driver of solid dissolution (See US2003/0180242 by Eccard W. E. et. al.).

Examples 20 through 22 demonstrate additional measured structural parameter values of the present invention. Example 20 which is representative of a predominantly open-celled porous solid of the present invention (produced from the processing mixture of Example 1 and producing fast dissolution as per Example 8) comprises a BET surface area of 0.056 m$^2$/g, a % open cells of 96.5% and a cell wall thickness of 0.112 mm. In contrast, Example 21 which is representative of a predominantly closed-celled porous solid and not of the present invention (produced from the processing mixture of Example 2 and producing poor dissolution as per Example 11) comprises a lower BET surface area of 0.026 m$^2$/g, a lower % open cells of 79.8% and a higher cell wall thickness of 0.156 mm. And, example 22 which is representative of a predominantly open-celled porous solid of the present invention, but with an identical solid composition as Example 21 (produced from the diluted processing mixture of Example 2 as per Example 3 and producing fast dissolution as per Example 14) comprises a higher BET surface area of 0.063 m$^2$/g, a higher % open cells of 94.1% and a lower cell wall thickness of 0.116 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited herein are incorporated herein by reference in their entirety; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process of making a personal care article comprising the steps of:
   d. preparing a pre-mix comprising surfactant, water soluble polymer, and optionally plasticizer, wherein said pre-mix has:
      i. from about 15% to 40% solids; and
   e. aerating said pre-mix by introducing a gas into the pre-mix to form a wet aerated pre-mix;
   f. forming the wet aerated pre-mix into a desired one or more shapes to form shaped wet pre-mix; and
   g. drying the shaped wet pre-mix to a desired final moisture content to form a flexible porous dissolvable solid structure article wherein the flexible porous dissolvable solid structure article has a % open cell content of from about 80% to about 100%, a specific surface area of from about 0.04 m$^2$/gram to about 0.19 m$^2$/gram, and a density of from about 0.06 g/cm$^3$ to about 0.10 g/cm$^3$.

2. The process according to claim 1 further comprising the step of cutting the flexible porous dissolvable solid structure article.

* * * * *